(12) United States Patent
Konno

(10) Patent No.: US 8,502,988 B2
(45) Date of Patent: Aug. 6, 2013

(54) PATTERN INSPECTION APPARATUS AND PATTERN INSPECTION METHOD

(75) Inventor: Yusaku Konno, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 411 days.

(21) Appl. No.: 12/835,271

(22) Filed: Jul. 13, 2010

(65) Prior Publication Data

US 2011/0063621 A1    Mar. 17, 2011

(30) Foreign Application Priority Data

Sep. 15, 2009  (JP) ................................ 2009-212887
Nov. 30, 2009  (JP) ................................ 2009-272132

(51) Int. Cl.
*G01B 11/02*   (2006.01)
*G01B 9/02*    (2006.01)

(52) U.S. Cl.
USPC ........................................ 356/491; 356/450

(58) Field of Classification Search
USPC .......... 356/491, 512, 364; 250/559; 430/311
See application file for complete search history.

(56) References Cited

U.S. PATENT DOCUMENTS

| | | | | |
|---|---|---|---|---|
| 5,838,433 A | * | 11/1998 | Hagiwara | 356/364 |
| 7,233,400 B2 | * | 6/2007 | Ueki | 356/497 |
| 7,457,548 B2 | * | 11/2008 | Tomaru | 398/161 |

FOREIGN PATENT DOCUMENTS

| | | |
|---|---|---|
| JP | 60-10104 | 1/1985 |
| JP | 63-200042 | 8/1988 |
| JP | 63-304179 | 12/1988 |
| JP | 2-24539 | 1/1990 |
| JP | 4-111336 | 4/1992 |
| JP | 7-286831 | 10/1995 |
| JP | 8-327557 | 12/1996 |
| JP | 8327557 | * 12/1996 |
| JP | 2004-101194 | 4/2004 |
| JP | 2007-147475 | 6/2007 |
| JP | 2008-14935 | 1/2008 |
| JP | 2009-516171 | 4/2009 |

OTHER PUBLICATIONS

U.S. Appl. No. 13/414,945, filed Mar. 8, 2012, Fujii, et al.
U.S. Appl. No. 13/423,877, filed Mar. 19, 2012, Konno, et al.
Japanese Office Action issued Sep. 8, 2011, in Patent Application No. 2009-272132. (with English-language translation).

* cited by examiner

*Primary Examiner* — Tarifur Chowdhury
*Assistant Examiner* — Sunghee Y Gray
(74) *Attorney, Agent, or Firm* — Oblon, Spivak, McClelland, Maier & Neustadt, L.L.P.

(57) ABSTRACT

According to one embodiment, a pattern inspection apparatus includes a light source, a beam splitter, a first optical system, a second optical system, a controller, a phase controller and a detector. The beam splitter splits an emitted light into first and second optical paths. The first optical system delivers the light to a first pattern and delivers a first reflected light from the first pattern. The second optical system delivers the light to a second pattern and delivers a second reflected light from the second pattern. The controller is provided on the optical path, and intensities of the first and second reflected lights are substantially equal. The phase controller is provided on the optical path, and phases of the first and second reflected lights are inverted. In addition, the detector detects a light that the first and second reflected lights are made to interfere with each other.

10 Claims, 12 Drawing Sheets

PATTERN INSPECTION APPARATUS AND PATTERN INSPECTION METHOD

CROSS-REFERENCE TO RELATED APPLICATIONS

This application is based upon and claims the benefit of priority from the prior Japanese Patent Application No. 2009-212887, filed on Sep. 15, 2009; No. 2009-272132, filed on Nov. 30, 2009; the entire contents of which are incorporated herein by reference.

FIELD

Embodiments described herein relate generally to a pattern inspection apparatus and a pattern inspection method.

BACKGROUND

In the fields of semiconductor devices, flat-panel displays, MEMSs, and the like, structures with microscopic patterns formed on their surfaces (hereafter, referred to as "microscopic structures") are manufactured by the lithography technique and the like. In recent years, smaller and more highly integrated microscopic structures have been manufactured. Along with such trends, the patterns formed on the surfaces of such microscopic structures have become finer.

Methods of inspecting such patterns include, for example, an inspection method called as the die-to-die inspection method. In this inspection method, firstly, identical patterns formed at different positions on the surface of an object to be inspected (hereafter, referred to as "workpiece") are detected by a detector. Then, the pieces of the detected data are compared to each other to find out whether there are or are not any defects or foreign objects (hereafter, simply referred to as "defects"). Unlike the die-to-database inspection method, the die-to-die inspection method does not need to create reference data from the design data (CAD data) in accordance to the pattern. Accordingly, the use of the die-to-die inspection method makes it possible to simplify the pattern inspection apparatus and the pattern inspection method.

As patterns become finer these days, defects formed in manufacturing processes have become more microscopic. Under such circumstances, if the size of a defect becomes smaller relative to the wavelength of the illuminating light, the amount of light scattered by the defect becomes smaller. As a result, a difference in the reflectance due to existence of a defect becomes smaller, so that the contrast is lowered.

To address this problem, a pattern inspection apparatus configured as follows has been proposed (refer to JP-A 8-327557 (Kokai)). The apparatus includes a view-field dividing unit, a shift-adjustment unit, and a defect highlighting unit. The view-field dividing unit divides an acquired optical image into two optical images which are laterally shifted from each other within the plane of the acquired image. The shift-adjustment unit laterally shifts the two optical images to superpose one upon the other. The defect highlighting unit detects a portion with defect by superposing the two optical images and thus optically deleting portions where there are no defects from the pattern.

The technique disclosed in JP-A 8-327557 (Kokai) uses the interference of the reflected lights with each other to delete the optical image corresponding to the portions without any defects. If any of the inspected patterns has a defect, the optical image corresponding to the portion with the defect remains undeleted. Thus, the apparatus of JP-A-8-327557 (Kokai) can check for defects.

According to the technique disclosed in FIG. 2 and the like of JP-A 8-327557 (Kokai), the beams of reflected light from different patterns are made to substantially coaxially enter. The beams of light thus having entered are divided into two optical images. Then the optical images are laterally shifted, and superposed one upon the other. The technique, however, has the following problems. The contrast corresponding to a microscopic defect may not be enhanced when the beams of reflected light entering substantially coaxially from the different patterns are divided with insufficient accuracy.

In addition, as disclosed in FIG. 11 of JP-A 8-327557 (Kokai), the apparatus is capable of detecting defects, but is incapable of increasing the intensities of light corresponding to the portions with defects. For this reason, the apparatus may fail to enhance the contrast corresponding to a microscopic defect.

Microscopic structures may have various defects. For example, each of the defects may differ in: type such as a short-circuited pattern, conduction, depletion, foreign objects remaining in the structure; material such as oxides, nitrides, metals, and semiconductors; and shape such as dimensions of the defects in the longitudinal and lateral directions. This causes a problem of variation in the wavelength and polarization of the light irradiating when the most appropriate contrast is to be obtained. Moreover, since the defects vary in type, material, and shape as described above, there are two types of defects: one which causes decrease in amount of reflected light thereby detected as a negative contrast; and the other which causes increase in amount of reflected light thereby detected as a positive contrast. In addition, since the defects vary in type, material, and shape as described above, beams of light may cancel off each other under certain interference conditions, and, as a result, the contrast may be lowered.

DETAILED DESCRIPTION

Figure 1:
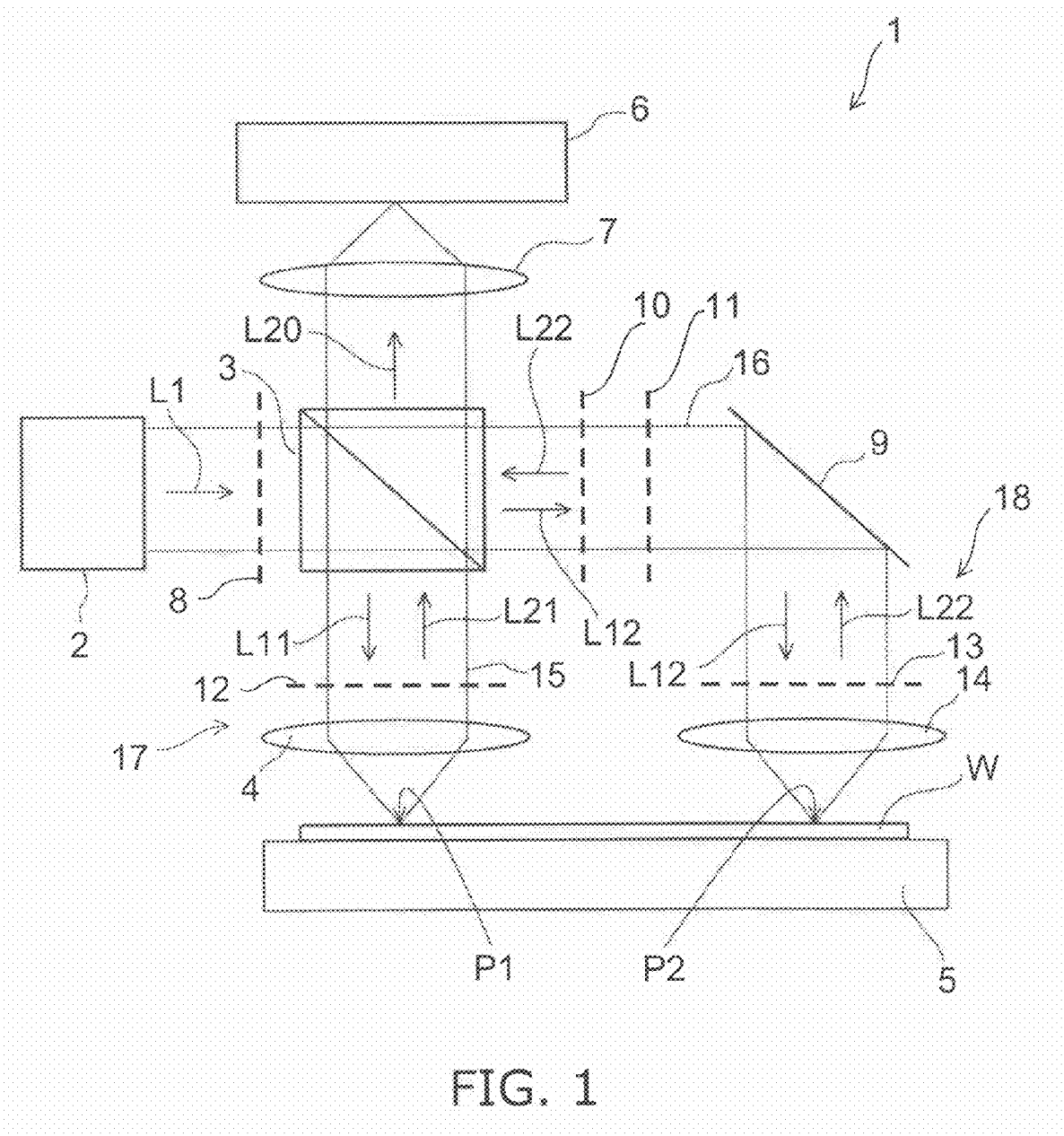
FIG. 1 is a schematic view illustrating a pattern inspection apparatus of a first embodiment.

In general, according to one embodiment, a pattern inspection apparatus includes a light source, a beam splitter, a first optical system, a second optical system, a controller, a phase controller and a detector. The beam splitter splits a light emitted from the light source into a first optical path and a second optical path. The first optical system is provided on the first optical path and the first optical system delivers the light to a first pattern and delivers a first reflected light from the first pattern. The second optical system is provided on the second optical path and the second optical system delivers the light to a second pattern and delivers a second reflected light from the second pattern, and the second pattern has an identical shape and dimensions to the first pattern. The controller is provided on at least one of the first optical path and the second optical path, and performs a control so that an intensity of the first reflected light and an intensity of the second reflected light are substantially equal to each other. The phase controller is provided on at least one of the first optical path and the second optical path, and performs a control so that a phase of the first reflected light and a phase of the second reflected light are inverted from each other. In addition, the detector detects a light produced by superposing the first reflected light and the second reflected light one upon the other in the beam splitter so that the first reflected light and the second reflected light are made to interfere with each other.

In general, according to another embodiment, a pattern inspection apparatus includes a light source, a beam splitter, a first polarization controller, a phase controller and a detector. The beam splitter generates a signal light and a reference light from a light emitted from the light source and the signal light is a reflected light from a pattern of an inspection target. The first polarization controller is capable of controlling a polarization angle and a polarization phase of the reference light. The phase controller is capable of controlling a phase of the reference light. In addition, the detector detects a light produced by superposing the signal light and the reference light so that the signal light and the reference light are made to interfere with each other.

In one embodiment, a method is disclosed for a pattern inspection. The method can split a light emitted from a light source into a first optical path and a second optical path. The method can generate a first reflected light from a first pattern being an inspection target by irradiating the first pattern with the light via the first optical path. The method can generate a second reflected light from a second pattern by irradiating the second pattern with the light via the second optical path and the second pattern has an identical shape and dimensions to the first pattern. The method can perform a control so that an intensity of the first reflected light is substantially equal to an intensity of the second reflected light, and that a phase of the first reflected light and a phase of the second reflected light are inverted from each other. The method can make the controlled first reflected light and the controlled second reflected light interfere with each other. In addition, the method can check existence of defects on the basis of an intensity of the interference light.

In another embodiment, a method is disclosed for a pattern inspection. The method can generate a signal light and a reference light from a light emitted from a light source and the signal light is a reflected light from a pattern of an inspection target. The method can control a polarization angle, a polarization phase, and a phase of the reference light. The method makes the signal light and the reference light interfere with each other. In addition, the method can check existence of defects on the basis of an intensity of the interference light.

Some embodiments will be described below by referring to the drawings. Constituent elements that appear across various drawings are denoted by the same reference numerals, and detailed description of such elements will be omitted.

FIG. 1 is a schematic view illustrating a pattern inspection apparatus of a first embodiment.

Figure 2:
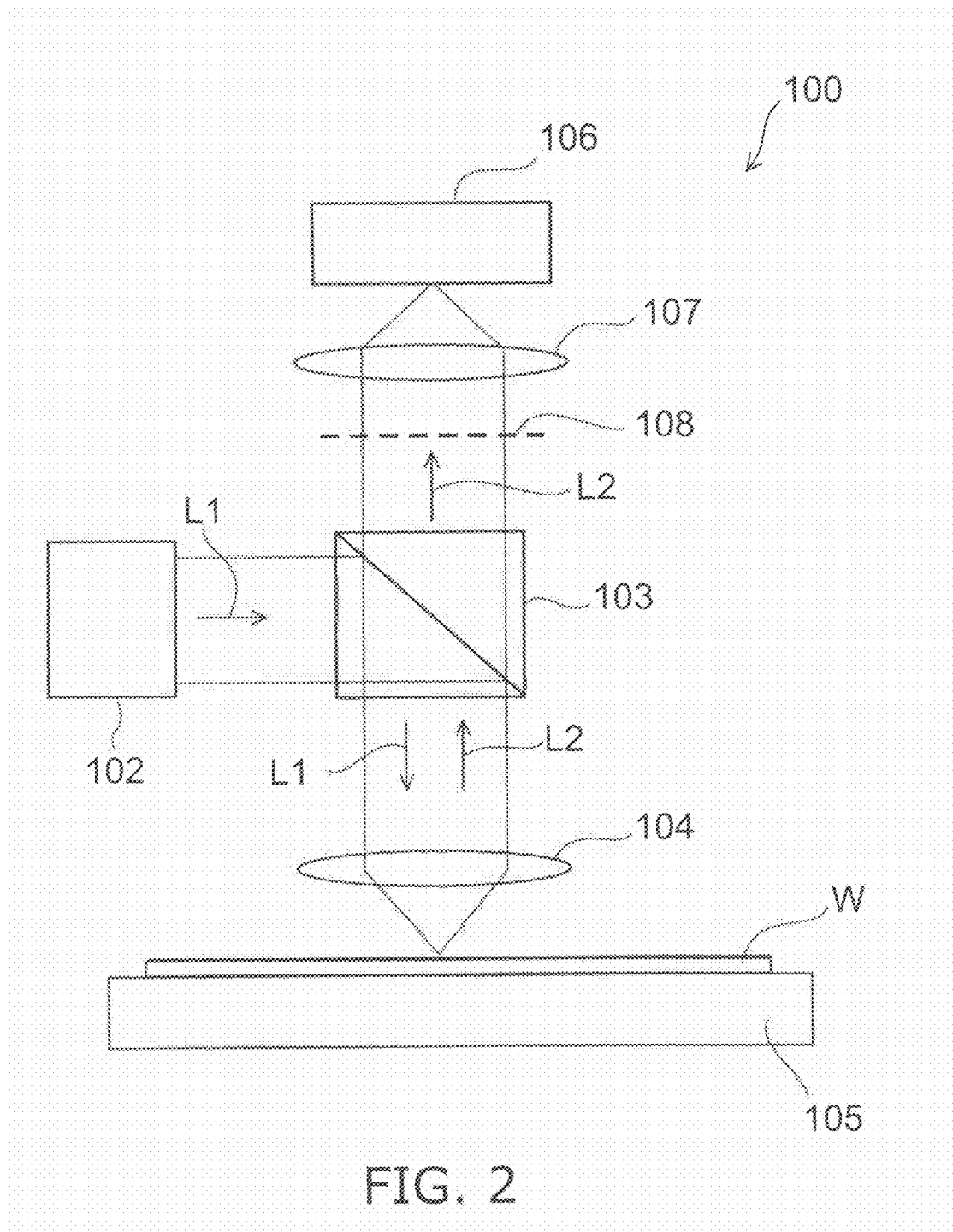
FIG. 2 is a schematic view illustrating a pattern inspection apparatus of a first comparative example.

FIG. 2 is a schematic view illustrating a pattern inspection apparatus of a first comparative example.

Figure 3:
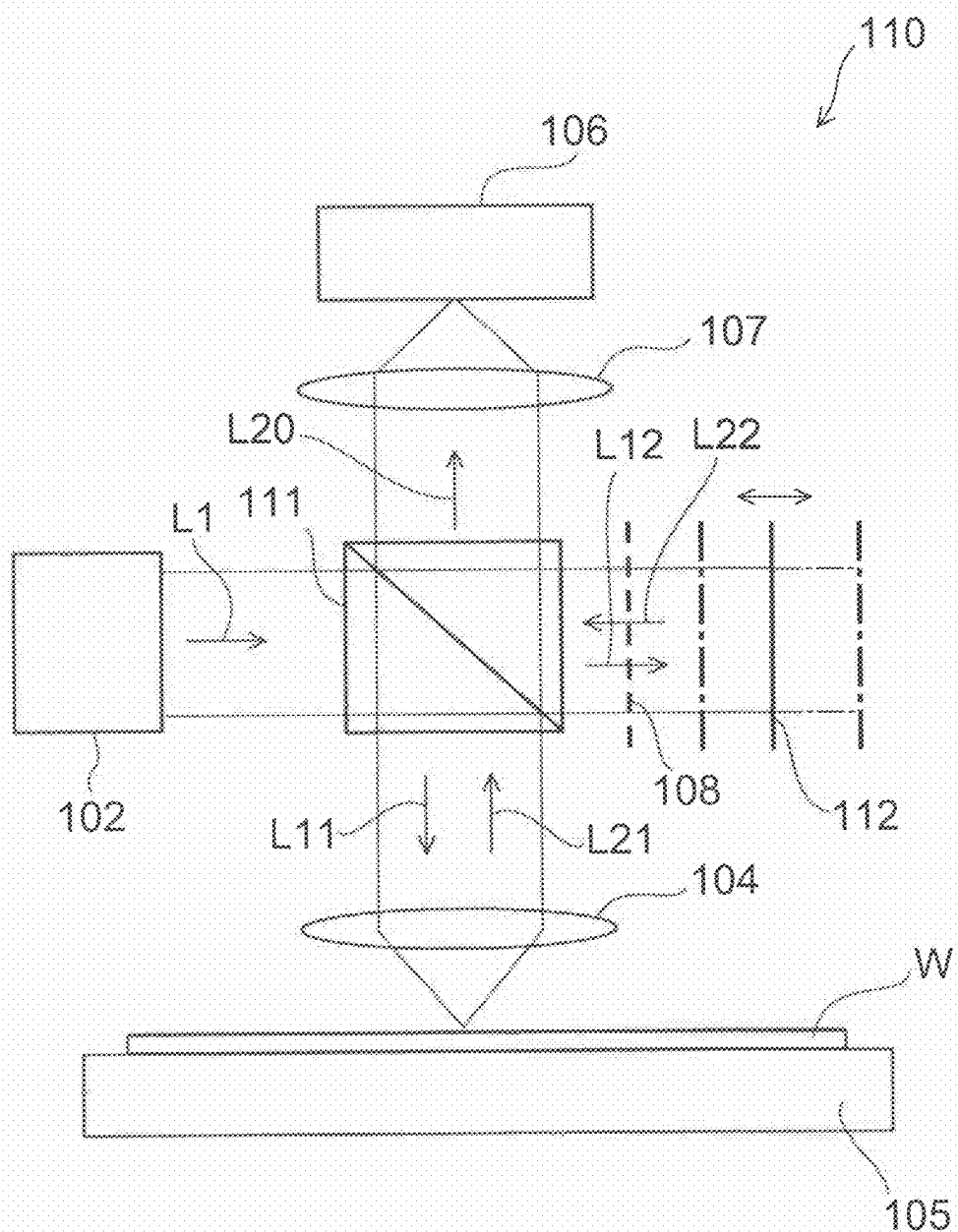
FIG. 3 is a schematic view illustrating a pattern inspection apparatus of a second embodiment.

FIG. 3 is a schematic view illustrating a pattern inspection apparatus of a second embodiment.

First of all, description will be given of a pattern inspection apparatus of a comparative example that the inventors examined during the development process of the invention. FIG. 2 shows a pattern inspection apparatus 100 of the first comparative example. The pattern inspection apparatus 100 includes a light source 102, a beam splitter 103, a mounting unit 105, and a detector 106. In addition, the pattern inspection apparatus 100 includes an object lens 104, an object lens 107, and a polarization controller 108, all of which are situated on the optical path.

The light source 102 may be a light source capable of emitting coherent beams of light. The beam splitter 103 reflects light L1 emitted from the light source 102 to deliver the light L1 onto a pattern formed on a workpiece W being the inspection target. Reflected light L2 from the pattern is allowed to pass through the beam splitter 103, and is then delivered to the detector 106. The mounting unit 105 is a place that the workpiece W is mounted on. The mounting unit 105 holds the workpiece W thus mounted, and changes the position of the workpiece W thus held. For example, the mounting unit 105 may be an XY table equipped with an electrostatic chuck (not illustrated). The detector 106 converts the light of an image formed on the light receiving surface of the detector 106 into electric signals.

The object lens 104 focuses the light L1 reflected by the beam splitter 103 onto the pattern formed on the workpiece W being the inspection target. The object lens 107 focuses the reflected light L2 that has passed through the beam splitter 103 onto the light receiving surface of the detector 106. To put it differently, the object lens 107 forms an optical image of the inspection target on the light receiving surface of the detector 106. The polarization controller 108 controls the polarization of the light passing through the polarization controller 108 so that the light is linearly polarized.

Next, description will be given of how the pattern inspection apparatus 100 operates.

Firstly, an unillustrated conveyor apparatus or an operator places the workpiece W on the mounting unit 105, and the mounting unit 105 holds the workpiece W. Then, the light source 102 emits the light L1, which is reflected by the beam splitter 103 and is then delivered onto the pattern formed on a workpiece W being the inspection target. In this event, the light L1 is condensed by the object lens 104 and the pattern formed on a workpiece W being the inspection target is irradiated with the light L1. The reflected light L2 from the pattern passes through the beam splitter 103, and is then subjected to the polarization control performed by the polarization controller 108. The reflected light L2 subjected to the polarization control by the polarization controller 108 is focused, by the object lens 107, onto the light receiving surface of the detector 106. To put it differently, an optical image of the inspection target is formed on the light receiving surface of the detector 106. The light of the optical image formed on the light receiving surface of the detector 106 is converted into electric signals, and thus the inspection data are acquired. Subsequently, the position to be inspected within the workpiece W mounted on the mounting unit 105 is changed to a different position. The inspection data for the new position are acquired in the above-described manner. On the basis of the inspection data thus acquired, existence of defects is checked. The existence of defects is checked by, for example, comparing the contrasts of the light of the acquired pieces of inspection data.

The pattern inspection apparatus 100 with the above-described configuration allows the user to check defects on the basis of the reflectance that varies depending on existence of defects. In recent years, however, as the patterns have become finer, the relative sizes of the defects to the wavelength of the illuminating light have become smaller. Accordingly, the amount of light scattered by the defect is decreased, and difference in reflectance between a case with defect and a case without defect becomes small. Consequently, the contrast is lowered, and such lower contrast may make it more difficult to check microscopic defects by use of the pattern inspection apparatus 100.

Next, description will be given of a pattern inspection apparatus 110 of the embodiment by referring to FIG. 3. FIG. 3 shows the pattern inspection apparatus 110 of the second embodiment. The pattern inspection apparatus 110 includes a light source 102, a beam splitter 111, a mounting unit 105, a detector 106, and a movable mirror (phase controller) 112. In addition, the pattern inspection apparatus 110 includes an object lens 104, an object lens 107, and a polarization controller 108, all of which are situated on the optical path.

The beam splitter 111 splits light L1 emitted from the light source 102 into two optical paths. The light L1 having reflected by the beam splitter 111 is delivered onto a pattern formed on a workpiece W being the inspection target. The light L1 having passed through the beam splitter 111 is delivered onto the movable mirror 112. Reflected light L21 from the pattern and reflected light L22 from the movable mirror 112 are superposed one upon the other, and are thus made to interfere with each other.

The movable mirror 112 includes a flat mirror. An unillustrated driving unit is provided to move the flat mirror in directions that are parallel to the optical axis. Moving the position of the flat mirror changes the optical path length. Thereby, the phase of the reflected light L22 is controlled.

Next, description will be given of how the pattern inspection apparatus 110 operates.

Firstly, an unillustrated conveyor apparatus or an operator places the workpiece W on the mounting unit 105, and the mounting unit 105 holds the workpiece W. Then, the light source 102 emits the light L1, which is split by the beam splitter 111. The light L11 having been reflected by the beam splitter 111 is then delivered onto the pattern formed on a workpiece W being the inspection target while the light L12 having passed through the beam splitter 111 is delivered onto the movable mirror 112. In this event, the light L11 is condensed by the object lens 104 whereas the light L12 is subjected to the polarization control performed by the polarization controller 108. The reflected light L21 from the pattern and the reflected light L22 from the movable mirror 112 are superposed one upon the other in the beam splitter 111. In this event, the position of the flat mirror of the movable mirror 112 is controlled to change the optical path length. Thus, the phase of the reflected light L22 is controlled so that the reflected light L21 and the reflected light L22 can interfere with each other. Light L20 (interference light) is focused by the object lens 107 onto the light receiving surface of the detector 106. To put it differently, an optical image of the inspection target whose contrast is enhanced by the interference is formed on the light receiving surface of the detector 106. The light of the optical image formed on the light receiving surface of the detector 106 is converted into electric signals, and thus the inspection data are acquired. Subsequently, the position to be inspected within the workpiece W mounted on the mounting unit 105 is changed to a different position. The inspection data for the new position are acquired in the above-described manner. On the basis of the inspection data thus acquired, existence of defects is checked. The existence of defects is checked by, for example, comparing the contrasts of the light of the acquired pieces of inspection data.

The pattern inspection apparatus 110 with the above-described configuration allows the contrast to be enhanced by the interference of the reflected lights L21 and L22 with each other. Accordingly, the user can check microscopic defects. Specific examples of the pattern inspection apparatus 110 of the second embodiment will be described in detail later.

Next, description will be given of a pattern inspection apparatus 1 of another embodiment of the invention by referring to FIG. 1.

FIG. 1 shows the pattern inspection apparatus 1, which includes a light source 2, a beam splitter 3, a mounting unit 5, and a detector 6. In addition, the pattern inspection apparatus 1 includes an object lens 4, an object lens 7, a polarization controller 8, a mirror 9, a polarization controller 10, a phase controller 11, a light-irradiation controller 12, a light-irradiation controller 13, and an object lens 14, all of which are situated on the optical path.

The light source 2 may be a light source capable of emitting coherent beams of light. Here, the light source 2 is preferably capable of emitting beams of light with short wavelengths in order to perform inspection on microscopic patterns. An example of such light sources is a YAG laser light source that emits beams of light with a wavelength of 266 nm. Note that the light source 2 is not limited only to laser light sources. An appropriate light source is selected by taking account of factors such as the size of the pattern.

The beam splitter 3 splits light L1 emitted from the light source 2 into a first optical path 15 and a second optical path 16. The ratio of intensities of the two resultant lights is set at 1:1 to make the two optical paths 15 and 16 receive lights with equal intensities. The light L11 having reflected by the beam splitter 3 is delivered onto a first pattern P1 formed on a workpiece W. The light L12 having passed through the beam splitter 111 is reflected by the mirror 9 and delivered onto a second pattern P2 formed on a workpiece W. Reflected light L21 (signal light) from the first pattern P1 on the workpiece W and reflected light L22 (reference light) from the second pattern P2 on the workpiece W are superposed one upon the other, and are thus made to interfere with each other. A specific example of the beam splitter 3 is a half mirror.

The mounting unit 5 is a unit that the workpiece W is mounted on, and holds the workpiece W. The mounting unit 5 is equipped with an unillustrated transfer unit, which is used to change the position of the workpiece W mounted on the mounting unit 5. By changing the position of the workpiece W, the area to be inspected can be changed. For example, the mounting unit 105 may be an XY table equipped with an electrostatic chuck (not illustrated). Note that the above-mentioned unillustrated transfer unit is not necessarily provided in the mounting unit 5. All that is necessary is to enable different areas within the workpiece to be subjected to the inspection.

The detector 6 converts the light of an image formed on the light receiving surface of the detector 6 into electric signals. In other words, the detector 6 detects the interference light L20 which is produced by superposing the reflected light L21 (signal light) and the reflected light L22 (reference light) in the beam splitter 3. In addition the detector 6 is placed so that the light receiving surface of the detector 6 and the surface on which the first pattern P1 and the second pattern P2 are formed are situated at optically conjugated positions. Charge coupled device (CCD) sensors, for example, are used as the detector 6. Various devices other than CCD sensors may also be used as long as the devices can convert the light of the image formed on the light receiving surface into electric signals.

The object lens 4 focuses the light L11 having been reflected by the beam splitter 3 onto the first pattern P1 on the workpiece W. The object lens 14 focuses the light L12 that has passed through the beam splitter 3 onto the second pattern P2 on the workpiece W. The object lens 7 focuses the light L20 from the beam splitter 3 onto the light receiving surface of the detector 6. To put it differently, the object lens 7 forms, on the light receiving surface of the detector 106, an optical image of the inspection target whose contrast is enhanced by the interference.

The polarization controller 8 controls the polarization (specifically, controls the polarization angle and polarization phase) of the light L1 emitted from the light source 2 so that the light L1 is linearly polarized. To be more specific, the polarization controller 8 is situated at a position on the optical path between the light source 3 and the beam splitter 3, and controls the light L1 emitted from the light source 3 so that the light L1 is linearly polarized. A wave plate, for example, may be used as the polarization controller 8.

The polarization controller 10 controls the polarization of the light (specifically, controls the polarization angle and polarization phase) that passes through the polarization controller 10.

The phase controller 11 controls the phase of the light that passes through the phase controller 11. Optical delay devices or the like may be used as the phase controller 11.

The control performed by the polarization controller 10 makes the intensity of the reflected light L21 (signal light) and the intensity of the reflected light L22 (reference light) substantially equal to each other. The control performed by the phase controller 11 makes the phase of the reflected light L21 (signal light) and the phase of the reflected light L22 (reference light) inverted from each other. The checking of microscopic defects can be done successfully if the difference between the intensity of the reflected light L21 (signal light) and the intensity of the reflected light L22 (reference light) is more than 5%.

Note that both the polarization controller 10 and the phase controller 11 are situated on the second optical path 16 in FIG. 1, but the polarization controller 10 and the phase controller 11 may be situated on at least one of the first optical path 15 and the second optical path 16.

The mirror 9 changes the direction in which the light L12 having passed through the beam splitter 3 is directed, and delivers the light L12 onto the second pattern P2 on the workpiece W.

The light-irradiation controller 12 situated on the first optical path 15 changes the position which is irradiated with the light L11 so that the first pattern P1 on the workpiece W can receive the light L11. The light-irradiation controller 13 situated on the second optical path 16 changes the position which is irradiated with the light L12 so that the second pattern P2 on the workpiece W can receive the light L12. In this event, the light-irradiation position is adjusted so that the second pattern P2 that has identical shape and dimensions to the first pattern P1 is appropriately irradiated with the light L12. Note that the first pattern P1 and the second pattern P2 may be formed in a single product, or in different products. Specifically, in the cases of semiconductor devices, the patterns P1 and P2 may be formed in a single cell or in a single chip (die). Alternatively, the patterns P1 and P2 may be formed separately in two different cells or chips (dies) that are adjacent to each other or that are separated from each other by a predetermined distance. Examples of the light-irradiation controller 12 and light-irradiation controller 13 include acoust optic modulator (AOM), galvanometer mirror, and polygon mirror. Besides these examples, devices that are capable of changing the light-irradiation position may be used.

In this embodiment, the object lens 4 forms a first optical system 17 provided on the first optical path 15. The first optical system 17 delivers the light L11 to the first pattern P1 and delivers the reflected light L21 from the first pattern P1 to the appropriate destination. The mirror 9 and the object lens 14 together form a second optical system 18 provided on the second optical path 16. The second optical system delivers the light L12 to the second pattern P2 with the identical shape and dimensions to the first pattern P1 and delivers the reflected light L22 from the second pattern P2 to the appropriate destination.

Next, description will be given of how the pattern inspection apparatus 1 operates.

Firstly, an unillustrated conveyor apparatus or an operator places the workpiece W on the mounting unit 5, and the mounting unit 5 holds the workpiece W. Then, the light source 2 emits the light L1, which is then linearly polarized by the control performed by the polarization controller 8. The light L1 thus linearly polarized is then split by the beam splitter 3 into the light L11 and the light L12. The ratio of the intensity of the light L11 to the intensity of the light L12 is, for example, 1:1. The light L11 having been reflected by the beam splitter 3 is then delivered onto the first pattern P1 on the workpiece W. In this event, the light-irradiation controller 12 controls the light-irradiation position so that the pattern being the inspection target can receive the light L11. In addition, the object lens 4 condenses the light L11.

In the meanwhile, the direction in which the light L12 advances after passing through the beam splitter 3 is changed by the mirror 9. The light L12 is thus delivered onto the second pattern P2 on the workpiece W. In this event, the light-irradiation controller 13 controls the light-irradiation position so that the second pattern P2 with the identical shape and dimensions to the first pattern P1 can receive the light L12. In addition, the object lens 14 condenses the light L12.

In addition, the polarization controller 10 performs the polarization control (control on the polarization angle and the polarization phase). The phase controller 11 performs the phase control. With these controls, the reflected light L21 (signal light) and the reflected light L22 (reference light) can have substantially equal intensities, and have inverted phases from each other. The checking of microscopic defects can be done successfully if difference between the intensity of the reflected light L21 (signal light) and the intensity of the reflected light L22 (reference light) is more than 5%.

Then, the reflected light L21 (signal light) from the first pattern P1 and the reflected light L22 (reference light) from the second pattern P2 are superposed one upon the other in the beam splitter 3. In this event, the reflected light L21 (signal light) and the reflected light L22 (reference light) are made to interfere with each other by the controls performed by the polarization controller 10 and the phase controller 11.

Note that the phase of the reflected light L21 (signal light) and the phase of the reflected light L22 (reference light) are inverted from each other. So, if the first pattern P1 and the second pattern P2 are identical to each other, that is, if there are no defects, the intensity of the light L20 produced by the superposing becomes significantly low. In contrast, if a portion of the first pattern P1 differs from the corresponding portion of the second pattern P2, that is, if there is a defect, an intensity and a phase of light in the portion with the defect changes. Consequently, the intensity of the light L20 produced by the superposing becomes higher.

The light L20 (interference light) produced by the superposing is focused by the object lens 7 onto the light receiving surface of the detector 6. To put it differently, an optical image of the inspection target is formed on the light receiving surface of the detector 6. The light of the optical image formed on the light receiving surface of the detector 6 is converted into electric signals, and thus the inspection data are acquired.

If the next position to be inspected is in an area which can not be irradiated with the light by the control performed by the light-irradiation controller 12 and the light-irradiation controller 13, the mounting unit 5 changes the position of the workpiece W and then the inspection data for the inspection position is acquired in the above-mentioned manner. In contrast, if the next position to be inspected is within the area which can be irradiated with the light by the control performed by the light-irradiation controller 12 and the light-emission irradiation controller 13, the light-irradiation controller 12 and the light-irradiation controller 13 changes the light-irradiation position and then the inspection data for the inspection position is acquired in the above-mentioned manner.

Subsequently, on the basis of the inspection data thus acquired, existence of defects is checked. The existence of defects is checked by, for example, comparing the contrasts of the light of the acquired pieces of inspection data.

According to this embodiment, the reflected lights L21 (signal light) and L22 (reference light) can be made to interfere with each other and thus the contrast can be enhanced. Note that the reflected light L22 (reference light) comes from the second pattern P2 that has identical shape and dimensions to the first pattern P1 being the inspection target. So, the control to cause the interference of the two lights L21 and L22 is easy. In other words, since the two reflected lights coming respectively from the two reflecting surfaces having identical properties are made to interfere with each other, the control on the phase and the amplitude (i.e., intensity of light) can be done more easily. Accordingly, the contrast can be enhanced furthermore, and the user can check more microscopic defects.

Figure 4:
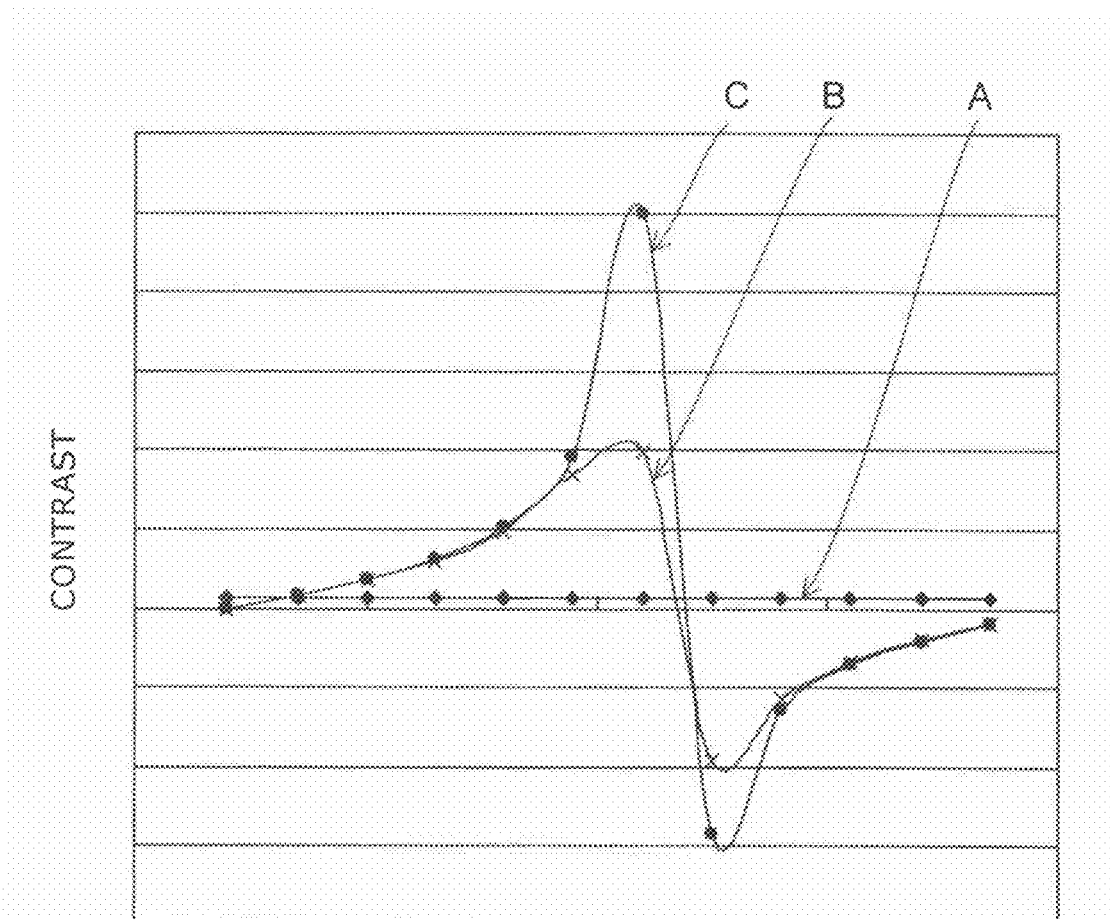
FIG. 4 is a graph schematically illustrating the differences in contrast.

FIG. 4 is a graph schematically illustrating the differences in contrast.

The A in FIG. 4 is of the case with the pattern inspection apparatus 100 shown in FIG. 2. The B in FIG. 4 is of the case with the pattern inspection apparatus 110 of the second embodiment. The C in FIG. 4 is of the case with the pattern inspection apparatus 1 of the first embodiment.

As the A in FIG. 4 shows, the contrast cannot be enhanced simply by detecting the reflected light from the pattern being the inspection target.

In contrast, both the pattern inspection apparatus 1 of the first embodiment and the pattern inspection apparatus 110 of the second embodiment can obtain higher contrast as shown in the C and B in FIG. 4. Consequently, more microscopic defects can be checked.

Figure 5:
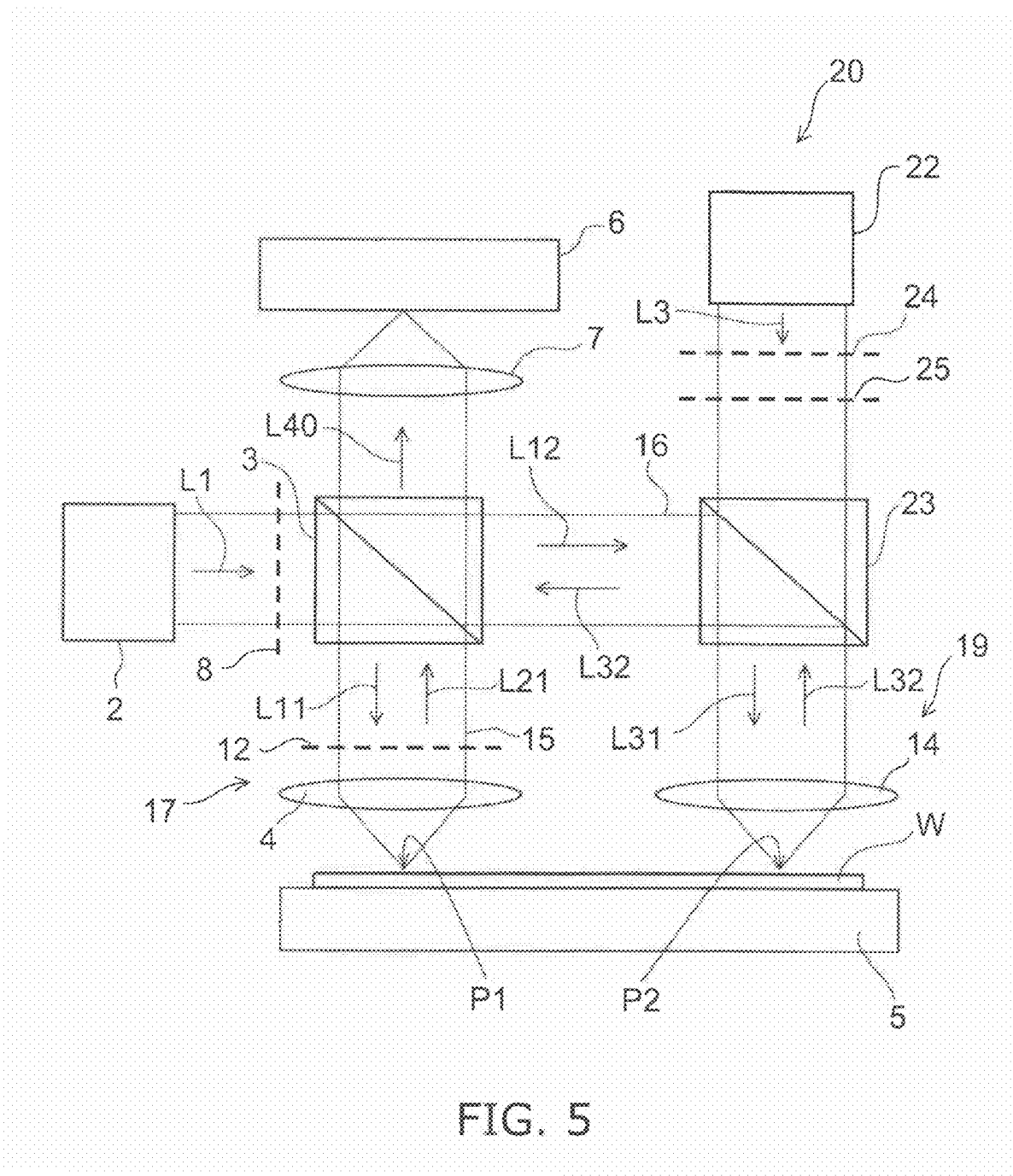
FIG. 5 is a schematic view illustrating a pattern inspection apparatus of a third embodiment.

FIG. 5 is a schematic view illustrating a pattern inspection apparatus of a third embodiment.

FIG. 5 shows a pattern inspection apparatus 20, which includes a light source 2, a beam splitter 3, a mounting unit 5, a detector 6, a light source 22, and a beam splitter 23. In addition, the pattern inspection apparatus 20 includes an object lens 4, an object lens 7, a polarization controller 8, a light-irradiation controller 12, an object lens 14, a polarization controller 24, and a phase controller 25, all of which are situated on the optical path.

Like the light source 2, the light source 22 may be a light source capable of emitting coherent beams of light. Here, the light source 22 is preferably capable of emitting beams of light with short wavelengths in order to perform inspection on microscopic patterns. An example of such light sources is a YAG laser light source that emits beams of light with a wavelength of 266 nm. Note that the light source 22 is not limited only to laser light sources. An appropriate light source is selected by taking account of factors such as the size of the pattern. In addition, both light L1 emitted from the light source 2 and light L3 emitted from the light source 22 are used for irradiation, as will be described in detail later. So, the light source 2 and the light source 22 are set to emit light with same frequency.

The beam splitter 23 allows the light L3 emitted from the light source 22 to pass through the beam splitter 23, and then delivers the light L3 onto a second pattern P2 formed on a workpiece W. Light L12, which is a part of light emitted from the light source 2 and then split by the beam splitter 3, is reflected by the beam splitter 23 thereby being delivered onto the second pattern P2 on the workpiece W. To put it differently, the second pattern P2 on the workpiece W receives both the light L12 emitted from the light source 2 and the light L3 emitted from the light source 22.

The polarization controller 24 controls the polarization (specifically, controls the polarization angle and polarization phase) of the light L3 emitted from the light source 22.

The phase controller 25 controls the phase of the light L3 emitted from the light source 22. Optical delay devices or the like may be used as the phase controller 25.

The control performed by the polarization controller 24 makes the intensity of reflected light L21 (signal light) and the intensity of reflected light L32 (reference light) substantially equal to each other. The control performed by the phase controller 25 makes the phase of the reflected light L21 (signal light) and the phase of the reflected light L32 (reference light) inverted from each other. The checking of microscopic defects can be done successfully if the difference between the intensity of the reflected light L21 (signal light) and the intensity of the reflected light L32 (reference light) is more than 5%.

Note that both the polarization controller 24 and the phase controller 25 are situated on the optical path between the light source 22 and the beam splitter 23 in FIG. 5, but the polarization controller 24 and the phase controller 25 may be situated on at least one of a first optical path 15 and a second optical path 16.

In this embodiment, the object lens 4 forms a first optical system 17 provided on the first optical path 15. The first optical system 17 delivers the light L11 to the first pattern P1 and delivers the reflected light L21 from the first pattern P1 to the appropriate destination. The beam splitter 23 and the object lens 14 together form a second optical system 19 provided on the second optical path 16. The second optical system 19 delivers the light L12 to the second pattern P2 with the identical shape and dimensions to the first pattern P1 and delivers the reflected light L32 from the second pattern P2 to the appropriate destination.

Next, description will be given of how the pattern inspection apparatus 20 operates.

Firstly, an unillustrated conveyor apparatus or an operator places the workpiece W on the mounting unit 5, and the mounting unit 5 holds the workpiece W. Then, the light source 2 emits the light L1, and the light source 22 emits the light L3.

The light L1 having been emitted from the light source 2 is then linearly polarized by the control performed by the polarization controller 8. The light L1 thus linearly polarized is then split by the beam splitter 3 into the light L11 and the light L12. The ratio of the intensity of the light L11 to the intensity of the light L12 is, for example, 1:1. The light L11 having been reflected by the beam splitter 3 is then delivered onto the first pattern P1 on the workpiece W. In this event, the light-irradiation controller 12 controls the light-irradiation position so that the pattern being the inspection target can receive the light L11. In addition, the object lens 4 condenses the light L11.

In the meanwhile, the light L12 having been passed through the beam splitter 3 is reflected by the beam splitter 23, and is then delivered onto the second pattern P2 on the workpiece W.

The light L3 emitted from the light source 22 passes through the beam splitter 23 and is then delivered onto the second pattern P2 on the workpiece W. Consequently, the second pattern P2 on the workpiece W receives light L31 produced by putting the light L12 and the light L3 together.

The light L31 is condensed by the object lens 14 and the second pattern P2 on the workpiece W is irradiated with the light L31. In this event, a particular second pattern P2 with the identical shape and dimensions to the first pattern P1 is irradiated with the light L31. To be more specific, a particular second pattern P2 being the fixed target is irradiated with the light L31 in this embodiment. This is because of the following reason. There may be a case where patterns with identical shape and dimensions are repeatedly formed such as in semiconductor memory devices. In this case, a pattern may be preferably selected as the above-mentioned particular second pattern P2, and the particular second pattern P2 is fixedly irradiated with the light L31. This allows elimination of the work for adjustments and controls which are needed if the second pattern P2 is changed from one pattern to another.

In this case, a pattern that has been proved nondefective in advance may preferably be selected as the particular second pattern P2 fixedly irradiated with the light L31. In this way, if a defect is detected by the inspection, which will be described in detail later, the user understands that the defect is in the first pattern P1.

Here, the light-irradiation controller 13 described in FIG. 1 may be provided, and a pattern may be selected as the particular second pattern P2 by controlling the light-irradiation controller 13. The pattern thus selected is then fixedly irradiated with the light L31.

In addition, the polarization controller 24 performs the polarization control (control on the polarization angle and the polarization phase) on the light L3 having been emitted from the light source 22. The phase controller 25 performs the phase control. With these controls, the reflected light L21 (signal light) and the reflected light L32 (reference light) can have substantially equal intensities, and have inverted phases from each other. The checking of microscopic defects can be done successfully if the difference between the intensity of the reflected light L21 (signal light) and the intensity of the reflected light L32 (reference light) is more than 5%.

The reflected light L32 (reference light) from the second pattern P2 is reflected by the beam splitter 23, and is then delivered to the beam splitter 3. In the beam splitter 3, the reflected light L21 (signal light) from the first pattern P1 and the reflected light L32 (reference light) from the second pattern P2 are superposed one upon the other. In this event, the reflected light L21 (signal light) and the reflected light L32 (reference light) are made to interfere with each other by the controls performed by the polarization controller 24 and the phase controller 25.

Note that the phase of the reflected light L21 (signal light) and the phase of the reflected light L32 (reference light) are inverted from each other. So, if the first pattern P1 and the second pattern P2 are identical to each other, that is, if there are no defects, the intensity of light L40 produced by the superposing of the lights L21 and L32 becomes significantly low. In contrast, if a portion of the first pattern P1 differs from the corresponding portion of the second pattern P2, that is, if there is a defect, an intensity and a phase of light in the portion with the defect changes. Consequently, the intensity of the light L40 produced by the superposing becomes higher.

The light L40 (interference light) produced by the superposing is focused by the object lens 7 onto the light receiving surface of the detector 6. To put it differently, an optical image of the inspection target is formed on the light receiving surface of the detector 6. The light of the optical image formed on the light receiving surface of the detector 6 is converted into electric signals, and thus the inspection data are acquired.

If the next position to be inspected is in an area which can not be irradiated with the light by the control performed by the light-irradiation controller 12, the mounting unit 5 changes the position of the workpiece W and then the inspection data for the inspection position is acquired in the above-mentioned manner. In contrast, if the next position to be inspected is within the area which can be irradiate with the light by the control performed by the light-irradiation controller 12, the light-irradiation controller 12 changes the light-irradiation position and then the inspection data for the inspection position is acquired in the above-mentioned manner.

Subsequently, on the basis of the inspection data thus acquired, existence of defects is checked. The existence of defects is checked by, for example, comparing the contrasts of the light of the acquired pieces of inspection data. Here, the second pattern P2 that has been proved nondefective in advance is irradiated with the light L31. Thus, if a defect is detected, the user understands that the defect is in the first pattern P1.

According to this embodiment, the reflected lights L21 (signal light) and L32 (reference light) can be made to interfere with each other and thus the contrast can be enhanced. Note that the reflected light L32 (reference light) comes from the second pattern P2 that has identical shape and dimensions to the first pattern P1 being the inspection target. So, the control to cause the interference of the two lights L21 and L32 is easy. In other words, since the two reflected lights coming respectively from the two reflecting surfaces having identical properties are made to interfere with each other, the control on the phase and the amplitude (i.e., intensity of light) can be done more easily.

In addition, both the light L1 emitted from the light source 2 and the light L3 emitted from the light source 22 are used for irradiation. Thus, the intensity of the light to be used for the inspection can be enhanced.

Accordingly, the contrast can be enhanced furthermore, and the user can check more microscopic defects.

In addition, the second pattern P2 that has been proved nondefective is irradiated with the light L31. Thus, if a defect is detected, the user can understand easily that the defect is in the first pattern P1.

Figure 6:
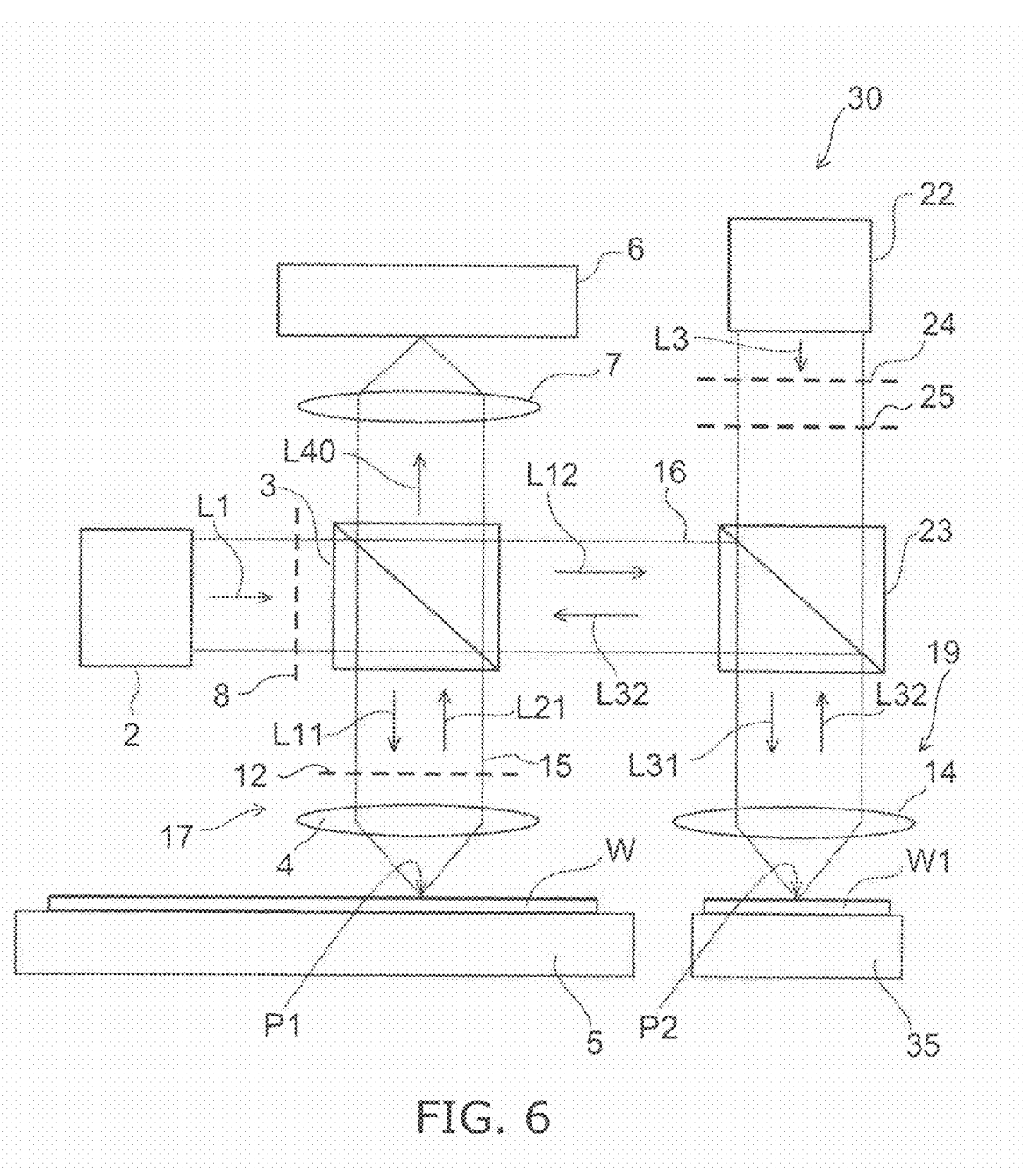
FIG. 6 is a schematic view illustrating a pattern inspection apparatus of a fourth embodiment.

FIG. 6 is a schematic view illustrating a pattern inspection apparatus of a fourth embodiment.

FIG. 6 shows a pattern inspection apparatus 30, which includes a light source 2, a beam splitter 3, a mounting unit 5, a detector 6, a light source 22, a beam splitter 23, and a holder unit 35. In addition, the pattern inspection apparatus 30 includes an object lens 4, an object lens 7, a polarization controller 8, a light-irradiation controller 12, an object lens 14, a polarization controller 24, and a phase controller 25, all of which are situated on the optical path.

The holder unit 35 holds a substrate W1 on which a second pattern P2 is formed. In this case, the second pattern P2 has identical shape and dimensions to a first pattern P1 being the inspection target. In addition, the second pattern P2 is a nondefective pattern. In addition, it is possible to form plural kinds of patterns on the substrate W1. In this case, the plural kinds of patterns differ from one another in shape and dimensions, and have no defects.

Some examples of the holder unit 35 are a mounting stage equipped with a built-in electrostatic chuck (not illustrated) and a frame-shaped member equipped with a holder frame. Note that these are not the only possible examples. Any member may be used as long as the member can hold the substrate W1 and allows the second pattern P2 formed on the substrate W1 to be irradiated with light.

Next, description will be given of how the pattern inspection apparatus 30 operates.

Note that some of the items similar to those described in the description of the pattern inspection apparatus 20 shown in FIG. 5 will not be described again in the following description.

Firstly, an unillustrated conveyor apparatus or an operator places the workpiece W on the mounting unit 5, and the mounting unit 5 holds the workpiece W. In addition, the holder unit 35 holds the substrate W1 on which the second pattern P2 is formed.

Then, the light source 2 emits the light L1, and the light source 22 emits the light L3.

Light L12, which is a part of light emitted from the light source 2 and then split by the beam splitter 3, is reflected by the beam splitter 23, and is then delivered onto the second pattern P2 formed on the substrate W1 held by the holder unit 35. The light L3 emitted from the light source 22 passes through the beam splitter 23 and is then delivered onto the second pattern P2 formed on the substrate W1. Consequently, the second pattern P2 on the substrate W1 receives light L31 produced by putting the light L12 and the light L3 together.

The light L31 is condensed by the object lens 14 and the second pattern P2 formed on the substrate W1 is fixedly irradiated with the light L31.

There may be a case where patterns with identical shape and dimensions are repeatedly formed, such as in semiconductor memory devices. In this case, the holder unit 35 holds a substrate W1 with the second pattern P2 that has been proved nondefective in advance, and the second pattern P2 is fixedly irradiated with the light L31. In this way, if a defect is detected by the inspection, which will be described in detail later, the user understands that the defect is in the first pattern P1.

Note that the light-irradiation controller 13 described in FIG. 1 may be provided, and the second pattern P2 formed on the substrate W1 may be used as the fixed target of the irradiation of the light L31 by controlling the light-irradiation controller 13. In addition if plural kinds of patterns are formed on the substrate W1, a pattern that has identical shape and dimensions to the first pattern P1 being the inspection target may be selected.

The reflected light L32 (reference light) from the second pattern P2 is reflected by the beam splitter 23, and is then delivered to the beam splitter 3. In the beam splitter 3, reflected light L21 (signal light) from the first pattern P1 and the reflected light L32 (reference light) from the second pattern P2 are superposed one upon the other. In this event, the reflected light L21 (signal light) and the reflected light L32 (reference light) are made to interfere with each other by the controls performed by the polarization controller 24 and the phase controller 25.

Note that the phase of the reflected light L21 (signal light) and the phase of the reflected light L32 (reference light) are inverted from each other. So, if the first pattern P1 and the second pattern P2 are identical to each other, that is, if there are no defects, the intensity of light L40 produced by the superposing of the lights L21 and L32 becomes significantly low. In contrast, if a portion of the first pattern P1 differs from the corresponding portion of the second pattern P2, that is, if there is a defect, an intensity and a phase of light in the portion with the defect changes. Consequently, the intensity of the light L40 produced by the superposing becomes higher.

The light L40 (interference light) produced by the superposing is focused by the object lens 7 onto the light receiving surface of the detector 6. To put it differently, an optical image of the inspection target is formed on the light receiving surface of the detector 6. The light of the optical image formed on the light receiving surface of the detector 6 is converted into electric signals, and thus the inspection data are acquired.

On the basis of the inspection data thus acquired, existence of defects is checked. The existence of defects is checked by, for example, comparing the contrasts of the light of the acquired pieces of inspection data. Here, the nondefective second pattern P2 formed on the substrate W1 is fixedly irradiated with the light L31. Thus, if a defect is detected, the user understands that the defect is in the first pattern P1.

According to this embodiment, the reflected lights L21 (signal light) and L32 (reference light) can be made to interfere with each other and thus the contrast can be enhanced. Note that the reflected light L32 (reference light) comes from the second pattern P2 that has identical shape and dimensions to the first pattern P1 being the inspection target. So, the control to cause the interference of the two lights L21 and L32 is easy. In other words, since the two reflected lights coming respectively from the two reflecting surfaces having identical properties are made to interfere with each other, the control on the phase and the amplitude (i.e., intensity of light) can be done more easily.

In addition, both the light L1 emitted from the light source 2 and the light L3 emitted from the light source 22 are used for irradiation. Thus, the intensity of the light to be used for the inspection can be enhanced.

Accordingly, the contrast can be enhanced furthermore, and the user can check more microscopic defects.

In addition, the nondefective second pattern P2 formed on the substrate W1 is fixedly irradiated with the light L31. Accordingly, if a defect is detected, the user can understand easily that the defect is in the first pattern P1.

Next, a pattern inspection method according to an embodiment of the invention will be described below.

Figure 7:
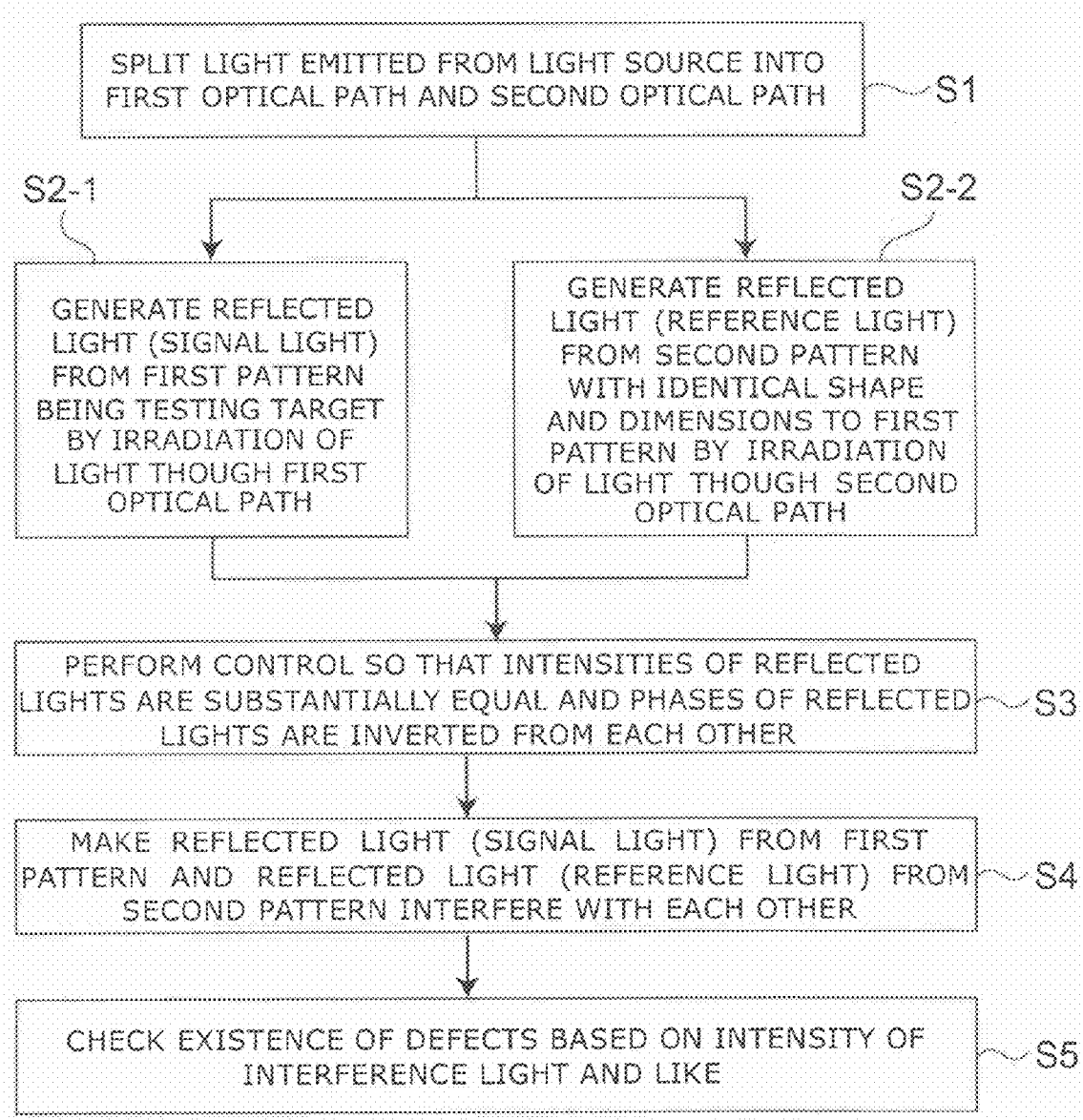
FIG. 7 is a flowchart illustrating the pattern inspection method of the embodiment.

FIG. 7 is a flowchart illustrating the pattern inspection method of the embodiment.

Firstly, light emitted from a light source is split into a first optical path and a second optical path (step S1).

Then, a first pattern P1 being the inspection target is irradiated with light though the first optical path. Reflected light (signal light) from the first pattern P1 is thus generated (step S2-1).

In the meanwhile, a second pattern P2 with identical shape and dimensions to the first pattern P1 is irradiated with light through the second optical path. Reflected light (reference light) from the second pattern P2 is thus generated (step S2-2).

In this event, the second pattern P2 may preferably be a pattern that has been proved nondefective in advance. In addition, the first pattern P1 may be formed on a workpiece W and the second pattern P2 may be formed not on the workpiece W but on a separate substrate W1.

Then, the following control is performed. The intensity of the reflected light (signal light) from the first pattern P1 is made substantially equal to the intensity of the reflected light (reference light) from the first pattern P2 while the phases of these reflected lights are inverted from each other (step S3).

In this event, the intensity and the phase of the reflected light from the second pattern P2 may preferably be controlled. In addition, if the control values of the intensities and the phases of the lights and the like are known in advance, at least one of the first pattern P1 and the second pattern P2 may be irradiated with light that has been controlled.

Subsequently, the reflected light (signal light) from the first pattern P1 and the reflected light (reference light) from the second pattern P2 are made to interfere with each other (step S4).

Then, on the basis of the intensity of the interference light and the like, existence of defects is checked (step S5).

According to this embodiment, the reflected light (signal light) from the first pattern P1 and the reflected light (reference light) from the second pattern P2 can be made to interfere with each other, and thus the contrast can be enhanced. Note that the reflected light (reference light) comes from the second pattern P2 that has identical shape and dimensions to the first pattern P1 being the inspection target. So, the control to cause the interference of the two reflected lights to is easy. In other words, since the two reflected lights coming respectively from the two reflecting surfaces having identical properties are made to interfere with each other, the control on the phase and the amplitude (i.e., intensity of light) can be done more easily.

Accordingly, the contrast can be enhanced furthermore, and the user can check more microscopic defects.

In addition, a pattern that has been proved nondefective in advance is used as the second pattern P2. Thus, if a defect is detected in the inspection, the user can understand easily that the defect is in the first pattern P1.

Next, description will be given of a specific example of the pattern inspection apparatus of the second embodiment.

Figure 8:
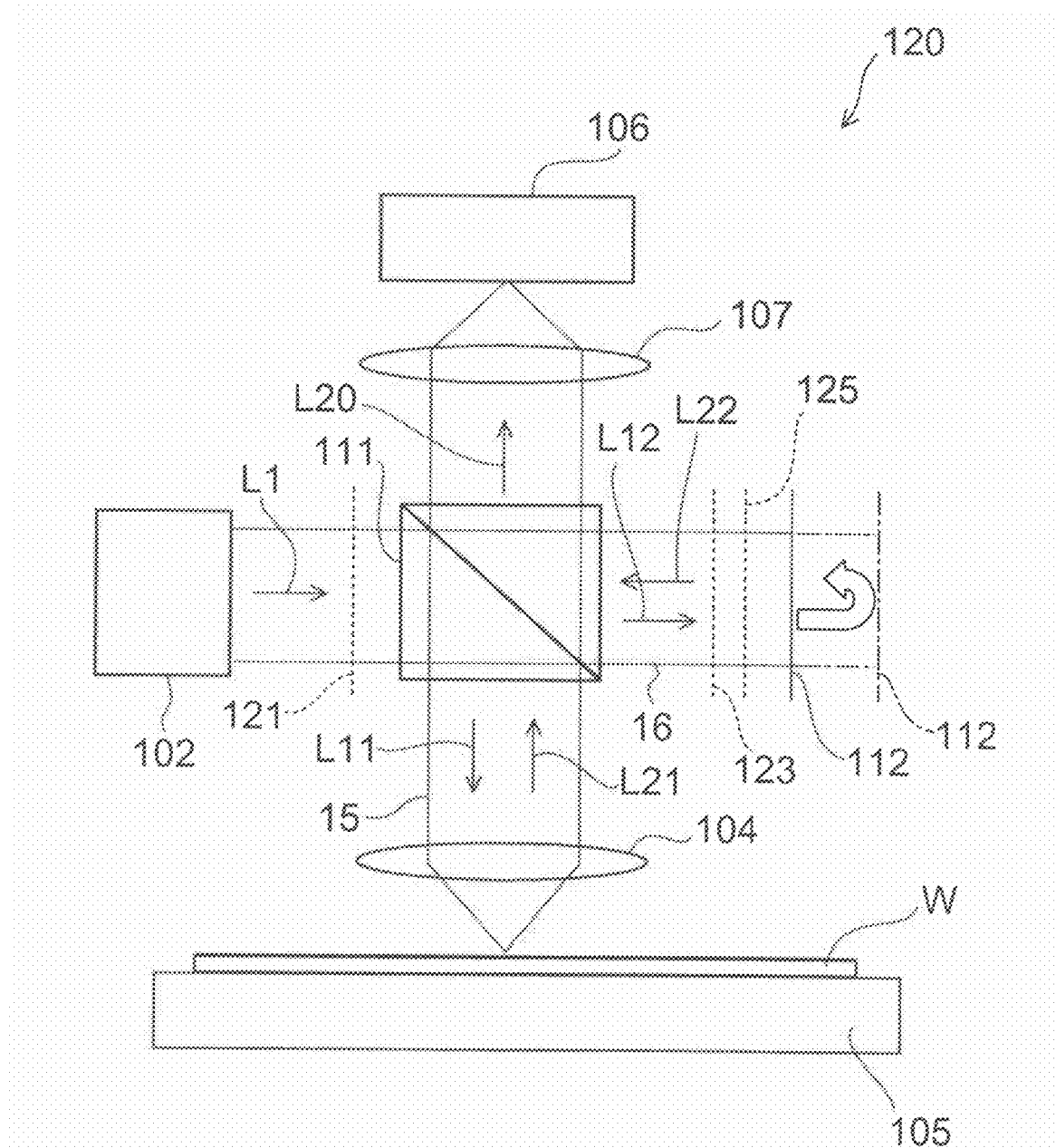
FIG. 8 is a schematic view illustrating the specific example of the pattern inspection apparatus of the second embodiment.

FIG. 8 is a schematic view illustrating the specific example of the pattern inspection apparatus of the second embodiment.

FIG. 8 shows a pattern inspection apparatus 120 of the specific example. The pattern inspection apparatus 120 includes a light source 102, a beam splitter 111, a mounting unit 105, a detector 106, and a movable mirror 112. In addition, the pattern inspection apparatus 120 includes an object lens 104, an object lens 107, a polarization controller 121 (a second polarization controller), a polarization controller 123 (a first polarization controller), and an intensity controller 125, all of which are situated on the optical path.

The polarization controller 121 controls the polarization (specifically, controls the polarization angle and polarization phase) of light L1 emitted from the light source 102 so that the light L1 is linearly polarized. To be more specific, the polarization controller 121 is situated at a position on the optical path between the light source 102 and the beam splitter 111, and controls the light L1 emitted from the light source 102 so that the light L1 is linearly polarized. A wave plate, for example, may be used as the polarization controller 121.

The polarization controller 123 is situated at a position on the optical path between the beam splitter 111 and the movable mirror 112, and controls the polarization of the light (specifically, controls the polarization angle and polarization phase) that passes through the polarization controller 123. As in the case of the polarization controller 121, a wave plate, for example, may be used as the polarization controller 123.

The intensity controller 125 is situated at a position on the optical path between the beam splitter 111 and the movable mirror 112, and controls the intensity of the light (specifically, controls the amplitude of the light) that passes through the intensity controller 125. A neutral density (ND) filter, for example, may be used as the intensity controller 125.

In the movable mirror 112, a flat mirror is moveable in directions parallel to the optical axis by use of, for example, a piezoelectric element. By moving the position of the flat mirror, the movable mirror 112 can change the optical path length. Thereby, the phase of the reflected light L22 can be controlled.

The rest of the structure is identical to that in the pattern inspection apparatus 110 described above by referring to FIG. 3. In addition, the light source 102, the mounting unit 105, the detector 106, the object lens 104, and the object lens 107 are identical respectively to the light source 2, the mounting unit 5, the detector 6, the object lens 4, and the object lens 7, all of which are described above by referring to FIG. 1.

Next, description will be given of how the pattern inspection apparatus 120 operates.

Firstly, an unillustrated conveyor apparatus or an operator places the workpiece W on the mounting unit 105, and the mounting unit 105 holds the workpiece W. Then, the light source 102 emits the light L1. Deep ultraviolet (DUV) laser light with a wavelength of 266 nm may be used as the light L1 emitted from the light source 102. The light L1 having been emitted from the light source 102 is then subjected to a control performed by the polarization controller 121 which linearly polarize the light. The linearly polarized light L1 is then split by the beam splitter 111 into light L11 and light L12. Specifically, the beam splitter 111 splits the light L1 having been emitted from the light source 102 into a first optical path 15 and a second optical path 16. The beam splitter 111 used at the optical branching passage may be either a beam splitter without polarization dependence or a polarizing beam splitter with polarization dependence. The light L11 having been reflected by the beam splitter 111 is then delivered onto a pattern on the workpiece W. In this event, the light-irradiation position is controlled using the mounting unit 105 so that the pattern being the inspection target can receive the light L11. In addition, the object lens 104 condenses the light L11.

In the meanwhile, the light L12 having passed through the beam splitter 111 is delivered to the movable mirror 112. In this event, the light L12 is subjected to a polarization control (control on the polarization angle and polarization phase) performed by the polarization controller 123, and to an intensity control (control on the amplitude) performed by the intensity controller 125. Then, the light L12 is reflected by the movable mirror 112. This reflected light L22 is delivered to the beam splitter 111. In this event, the position of the flat mirror in the movable mirror 112 is controlled to change the optical pathlength, thereby controlling the phase of the reflected light L22.

Then, the reflected light L21 (signal light) from the pattern and the reflected light L22 (reference light) from the movable mirror 112 are superposed one upon the other in the beam splitter 111. Note that the reflected light L21 (signal light) interferes with the reflected light L22 (reference light) which is subjected to a polarization control performed by the polarization controller 123, an intensity control performed by the intensity controller 125, and a phase control performed by the movable mirror 112.

The workpiece W may have various defects. For example, each of the defects may differ in: type such as a short-circuited pattern, conduction, depletion, foreign objects remaining in the structure; material such as oxides, nitrides, metals, and semiconductors; and shape such as dimensions in the longitudinal and lateral directions. The polarization angle and polarization phase of the light L1 emitted from the light source 102 are controlled appropriately on the basis of the above-mentioned differences. In addition, the polarization angle, polarization phase, intensity, and phase of the reflected light L22 (reference light) are controlled appropriately to enhance the contrast between the defective portions and the nondefective portions on the basis of the above-mentioned differences in type, material, and shape among defects. Accordingly, the contrast concerning the defects can be enhanced. In addition, the enhanced contrast can be obtained by a single inspection.

Alternatively, the polarization angle and polarization phase of the light L1 emitted from the light source 102 and the polarization angle, polarization phase, intensity, and phase of the reflected light L22 (reference light) may be controlled appropriately to enhance the contrast concerning the defects irrespective of the above-mentioned difference in types, materials, and shapes among defects. Accordingly, the contrast can be enhanced irrespective of the type, the material, and the shape of defect.

Still alternatively, the polarization angle and polarization phase of the light L1 emitted from the light source 102 and the polarization angle, polarization phase, intensity, and phase of the reflected light L22 (reference light) may be controlled appropriately to enhance the contrast concerning the defects irrespective of the height of the pattern formed on the workpiece W. Accordingly, the contrast can be enhanced irrespective of the height of the pattern formed on the workpiece W.

Still alternatively, the polarization angle, polarization phase, intensity, and phase of the reflected light L22 (reference light) may be controlled appropriately to minimize the intensity of the reflected light L21 (signal light) from nondefective portions. The defects of the workpiece W may be different in type, material, and shape as described above. These defects can be categorized into two types: one which cause decrease in amount of reflected light thereby detected as a negative contrast; and the other which cause increase in amount of reflected light thereby detected as a positive contrast. Considering this, the polarization angle, polarization phase, intensity, and phase of the reflected light L22 (reference light) are controlled appropriately to minimize the intensities of the reflected light L21 (signal light) from nondefective portions. Accordingly, the contrast concerning the defect can be always kept at a positive value. The above control eliminates such conditions where both positive and negative contrasts exist in a mixed manner due to defects which differ in type, material, and shape as described above, or where the contrast is significantly lowered due to certain light-interference conditions. In addition, the above control allows the detected contrasts to be always positive.

Light L20 (interference light) produced by the superposition of the reflected lights L21 and L22 is focused by the object lens 107 onto the light receiving surface of the detector 106. Note that the light receiving surface of the detector 106 is situated at an optically conjugated position to the workpiece W. An optical image of the inspection target is thus formed on the light receiving surface of the detector 106. The light of the optical image formed on the light receiving surface of the detector 106 is converted into electric signals, and thus the inspection data are acquired. Subsequently, the position to be inspected within the workpiece W mounted on the mounting unit 105 is changed to a different position. The inspection data for the new position are acquired in the above-described manner. On the basis of the inspection data thus acquired, existence of defects is checked. The existence of defects is checked by, for example, comparing the contrasts of the light of the acquired pieces of inspection data.

There are several ways of acquiring inspection data (contrast). For example, the contrast between defective portions and nondefective portions is acquired using, as the detector 106, an array-type imaging device with a spatial resolution. Alternatively, an imaging device with a spatial resolution or a photomultiplier tube without a spatial resolution is used as the detector 106, and the contrast between defective portions and nondefective portions is acquired by scanning the workpiece W or by irradiation of the light on the workpiece by use of the detector 106. These ways of acquiring inspection data (contrast) can be adopted in another specific example to be described later by referring to FIG. 9.

According to this specific example, as described earlier in this section, the polarization angle, the polarization phase of the light L1 emitted from the light source 102, and the polarization angle, polarization phase, intensity, and phase of the reflected light L22 (reference light) are controlled appropriately. So, the contrast concerning a microscopic defect can be enhanced. In addition, the enhancing of the contrast is possible irrespective of the type, material, shape, and the like of a defect. Consequently, more microscopic defects can be checked.

Figure 9:
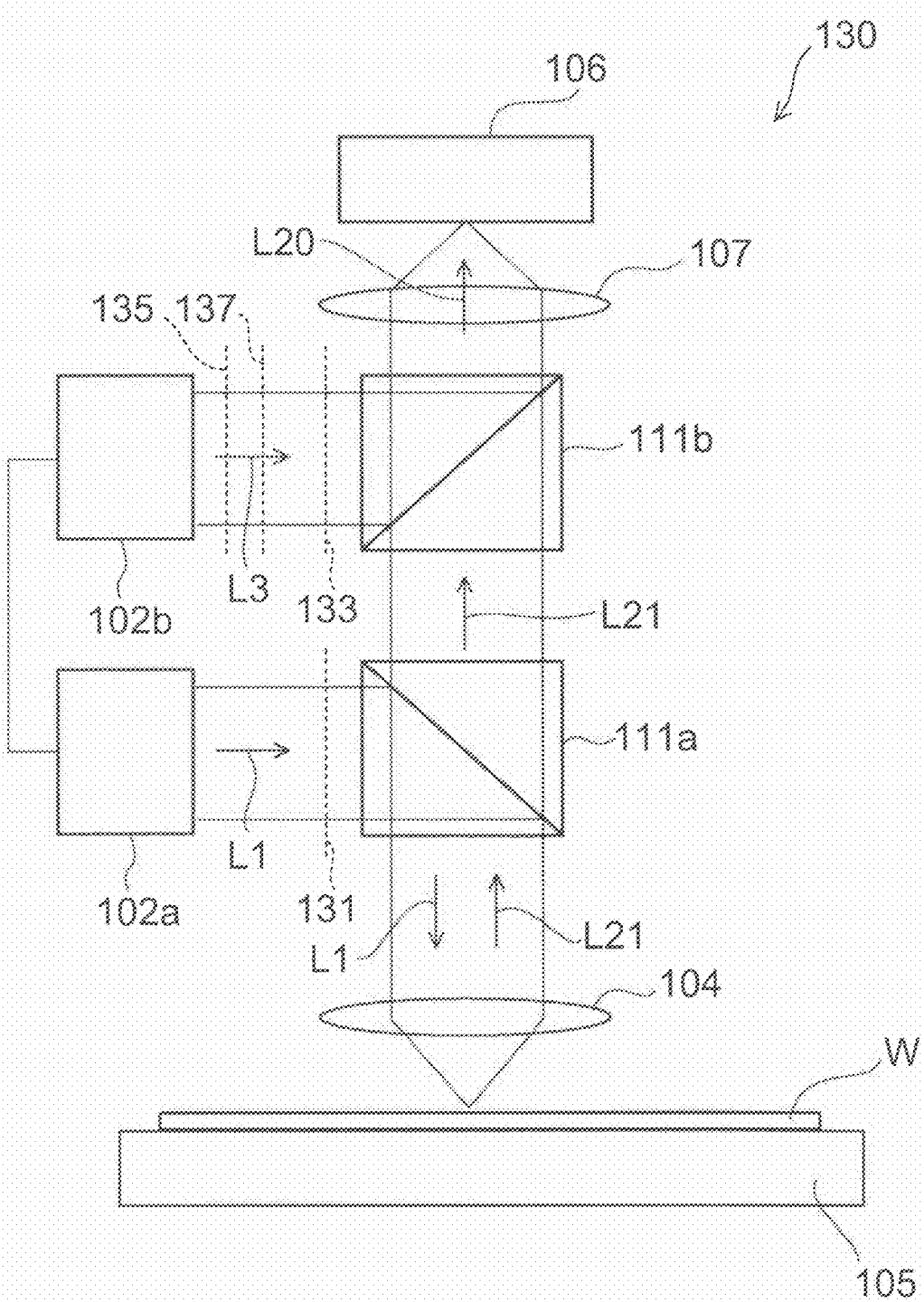
FIG. 9 is a schematic view illustrating another specific example of the pattern inspection apparatus of the second embodiment.

FIG. 9 is a schematic view illustrating another specific example of the pattern inspection apparatus of the second embodiment.

A way of superposing the signal light from the pattern onto the reference light that has been subjected to a polarization control (control on the polarization angle and polarization phase), an intensity control (control on the amplitude), and a phase control is not limited only to one described earlier in the specific example shown in FIG. 8. Instead of splitting the light emitted from a single light source into two optical paths, for example, lights emitted respectively from two different light sources may be superposed on each other as in the second specific example shown in FIG. 9.

To be more specific, FIG. 9 shows a pattern inspection apparatus 130 of the second specific example. The pattern inspection apparatus 130 includes a light source 102a, a light source 102b, a beam splitter 111a, a beam splitter 111b, a mounting unit 105, and a detector 106. In addition, the pattern inspection apparatus 130 includes an object lens 104, an object lens 107, a polarization controller 131 (a second polarization controller), a polarization controller 133 (a first polarization controller), an intensity controller 135, and a phase controller 137, all of which are situated on the optical path.

The polarization controller 131 controls the polarization (specifically, controls the polarization angle and polarization phase) of light L1 emitted from the light source 102a so that the light L1 is linearly polarized. To be more specific, the polarization controller 131 is situated at a position on the optical path between the light source 102a and the beam splitter 111a, and controls the light L1 emitted from the light source 102a so that the light L1 is linearly polarized. A wave plate, for example, may be used as the polarization controller 131.

The polarization controller 133 is situated at a position on the optical path between the light source 102b and the beam splitter 111b, and controls the polarization of the light (specifically, controls the polarization angle and polarization phase) that passes through the polarization controller 133. As in the case of the polarization controller 131, a wave plate, for example, may be used as the polarization controller 133.

The intensity controller 135 is situated at a position on the optical path between the light source 102b and the beam splitter 111b, and controls the intensity of the light that passes through the intensity controller 135. A neutral density (ND) filter, for example, may be used as the intensity controller 135.

The phase controller 137 is situated at a position on the optical path between the light source 102b and the beam splitter 111b, and controls the phase of the light that passes through the phase controller 137. An optical delay device, for example, may be used as the phase controller 137.

The mounting unit 105, the detector 106, the object lens 104, and the object lens 107 are identical respectively to the mounting unit 5, the detector 6, the object lens 4, and the object lens 7, all of which are described above by referring to FIG. 1.

Next, description will be given of how the pattern inspection apparatus 130 operates.

Firstly, an unillustrated conveyor apparatus or an operator places the workpiece W on the mounting unit 105, and the mounting unit 105 holds the workpiece W. Then, the light source 102a emits the light L1, and the light source 102b emits light L3. Note that, as will be described later, the light L1 emitted from the light source 102a and the light L3 emitted from the light source 102b are made to interfere with each other. So, the light source 102a and the light source 102b emit light with the same frequency.

The light L1 having been emitted from the light source 102a is reflected by the beam splitter 111a, and is then delivered onto the pattern formed on the workpiece W. In this event, the light irradiation-position is controlled using the mounting unit 105 so that the pattern being the inspection target can receive the light L1 appropriately. In addition, the object lens 104 condenses the light L1.

On the other hand, the light L3 emitted from the light source 102b is delivered to the beam splitter 111b. In this event, the light L3 is subjected to a polarization control (control on the polarization angle and polarization phase) performed by the polarization controller 133, an intensity control (control on the amplitude) performed by the intensity controller 135, and a phase control performed by the phase controller 137.

Subsequently, reflected light L21 (signal light) from the pattern and the light L3 (reference light) emitted from the light source 102b are superposed one upon the other in the beam splitter 111b. In this event, the reflected light L21 (signal light) is made to interfere with the light L3 (reference light) which is subjected to the polarization control performed by the polarization controller 133, the intensity control performed by the intensity controller 135, and the phase control performed by the phase controller 137.

In this event, the polarization angle and polarization phase of the light L1 emitted from the light source 102a and the polarization angle, polarization phase, intensity, and phase of the light L3 (reference light) emitted from the light source 102b are controlled appropriately to enhance the contrast. Alternatively, the polarization angle, polarization phase, intensity, and phase of the reflected light L3 (reference light) emitted from the light source 102b may be controlled appropriately to minimize the intensity of the reflected light L21 (signal light) from nondefective portions. Accordingly, the same effects as those described above by referring to FIG. 8 can be obtained.

Light L20 (interference light) produced by the superposition of the lights L21 and L3 is focused by the object lens 107 onto the light receiving surface of the detector 106. Note that the light receiving surface of the detector 106 is situated at an optically conjugated position to the workpiece W. An optical image of the inspection target is thus formed on the light receiving surface of the detector 106. The light of the optical image formed on the light receiving surface of the detector 106 is converted into electric signals, and thus the inspection data are acquired. Subsequently, the position to be inspected within the workpiece W mounted on the mounting unit 105 is changed to a different position. The inspection data for the new position are acquired in the above-described manner. On the basis of the inspection data thus acquired, existence of defects is checked. The existence of defects is checked by, for example, comparing the contrasts of the light of the acquired pieces of inspection data.

According to this specific example, as described earlier, the polarization angle, the polarization phase of the light L1 emitted from the light source 102a and the polarization angle, polarization phase, intensity, and phase of the light 3 emitted from the light source 102b are controlled appropriately. So, the contrast concerning a microscopic defect can be enhanced. In addition, the enhancing of the contrast is possible irrespective of the type, material, shape, and the like of a defect. Consequently, more microscopic defects can be checked.

Subsequently, description will be given of a case where a microscopic structure has a conduction defect and the contrast concerning the conduction defect is numerically calculated.

Figure 10:
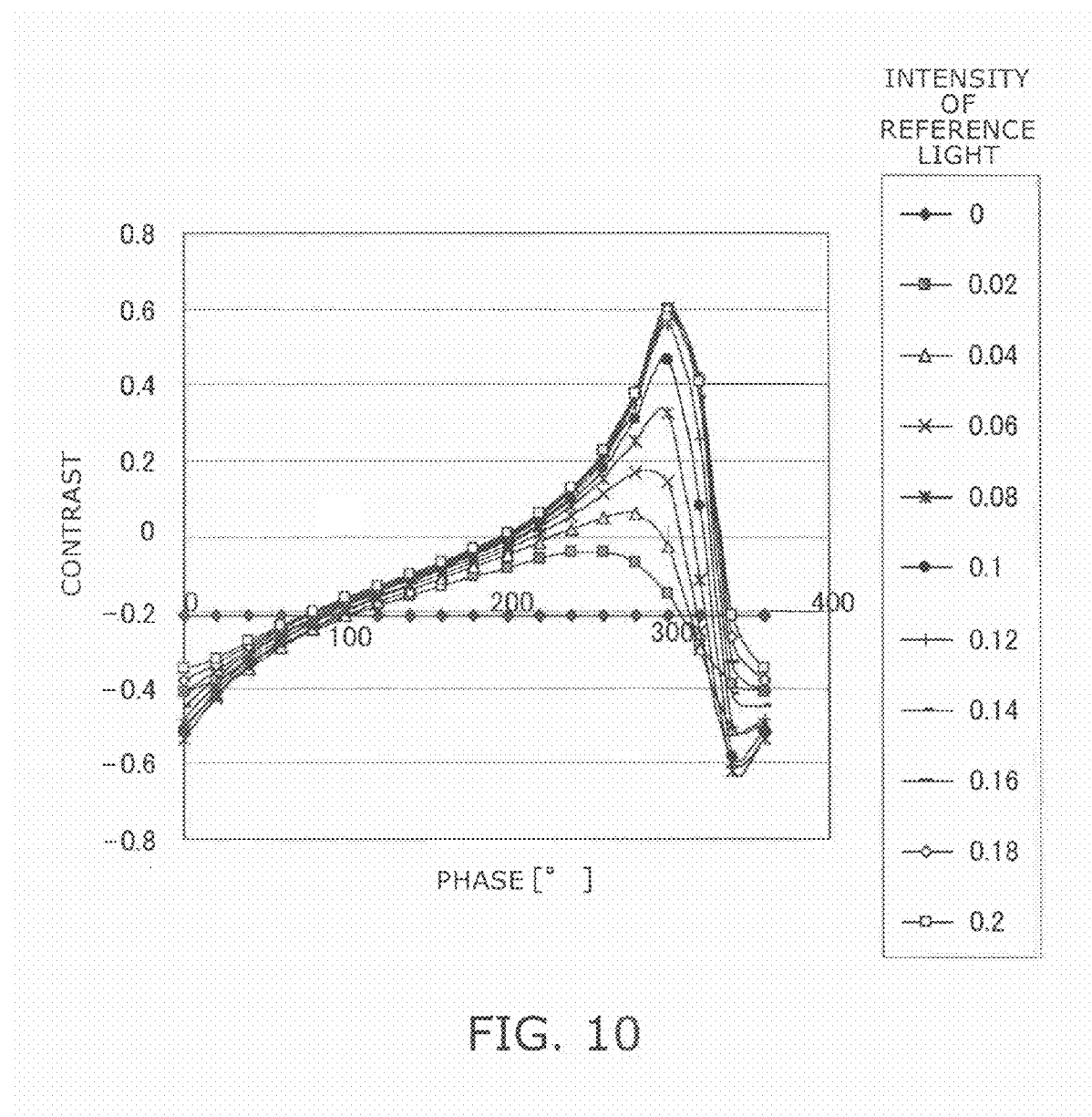
FIG. 10 is a schematic graph illustrating the calculation results of a case where a microscopic structure has a conduction defect and the contrast concerning the conduction defect is numerically calculated.

FIG. 10 is a graph illustrating the calculation results of a case where a microscopic structure has a conduction defect and the contrast concerning the conduction defect is numerically calculated.

The numerical calculation is based on an assumption that a conduction defect occurs in a multilayer-film line pattern made of a dielectric material and a metal and formed on a substrate. The chart of FIG. 10 shows an example of results showing how the contrast between the reflectance R1 of light from nondefective place and the reflectance R2 of light from defective place changes depending on the intensity and the phase of the reference light. The vertical axis of the chart shown in FIG. 10 represents the contrast whereas the horizontal axis represents the phase difference between the signal light and the reference light. The contrast is given by (R2−R1)/(R2+R1).

According to FIG. 10, if the intensity of the reference light is zero, that is, if the signal light and the reference light do not interfere with each other, the contrast is approximately −0.2. In contrast, if the intensity and the phase of the reference light are controlled appropriately as in the cases described above by referring to FIGS. 8 and 9, a contrast of approximately 0.6 or of approximately −0.6 can be obtained. Accordingly, the contrast that can be obtained if the intensity and the phase of the reference light are controlled appropriately is higher than the contrast obtained when the intensity of the reference light is zero. Consequently, nondefective places and defective places can be compared more easily from the contrast therebetween, and more microscopic defects can be checked.

Subsequently, description will be given of a case where a microscopic structure has both a conduction defect and a short-circuit defect in a mixed manner and the contrasts are numerically calculated.

Figure 11:
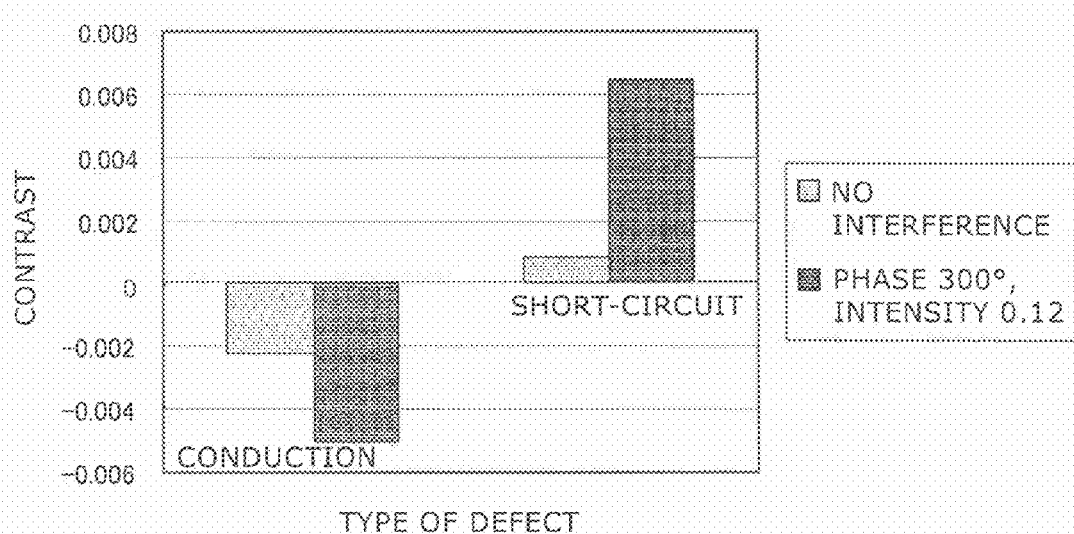
FIG. 11 is a schematic graph illustrating the calculation results of a case where a microscopic structure has both a conduction defect and a short-circuit defect existing in a mixed manner, and the contrasts are numerically calculated.

FIG. 11 is a graph illustrating the calculation results of a case where a microscopic structure has both a conduction defect and a short-circuit defect existing in a mixed manner, and the contrasts are numerically calculated.

The graph shown in FIG. 11 shows an example of a result where the contrasts concerning a conduction defect and the contrasts concerning a short-circuit defect are compared. For each type of defect, two contrasts are shown: one in a case where the signal light and the reference light are not made to interfere with each other; and the other in a case where the signal light and the reference light are made to interfere with each other.

For the case where the signal light and the reference light are made to interfere with each other, the inspection is conducted once with the polarization angle, polarization phase, intensity, and phase of the reference light being set to be optimal to the same incident polarization conditions. Specifically, in this numerical calculation, the intensity of the reference light is set at 0.12, and the phase difference between the signal light and the reference light is set at 300°.

For the case where the signal light and the reference light are not made to interfere with each other, the inspection is conducted twice with different optimal incident polarization conditions.

According to FIG. 11, higher contrasts can be obtained both for the conduction defect and for the short-circuit defect when the signal light and the reference light are made to interfere with each other. In addition the contrasts can be obtained by a smaller number of inspections. This means that a higher contrast can be obtained irrespective of the type of the defect. Accordingly, more microscopic defects can be checked irrespective of the type of the defect.

Subsequently, description will be given of a case where a microscopic structure has conduction defects with different heights and the contrasts are numerically calculated.

Figure 12:
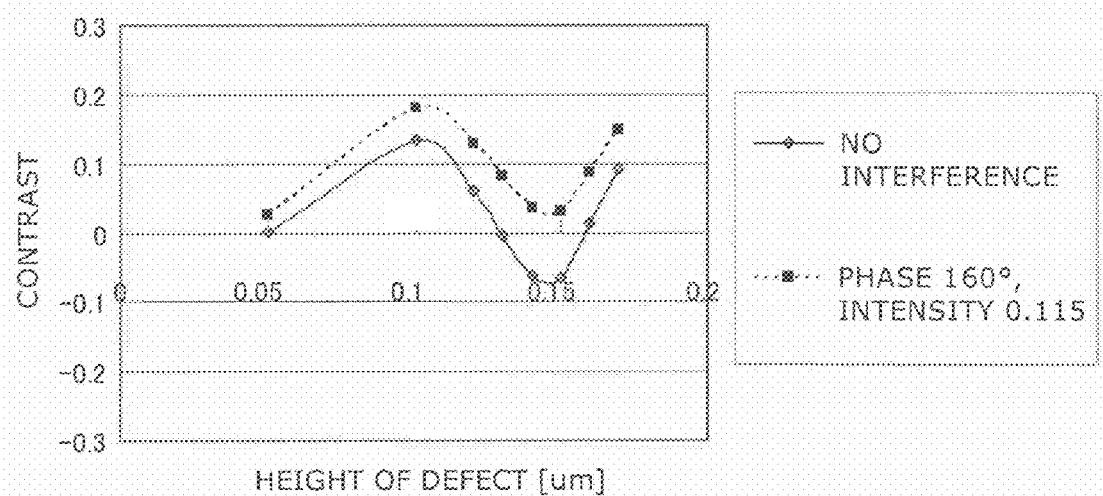
FIG. 12 is a schematic graph illustrating the calculation results of a case where a microscopic structure has conduction defects with different heights and the contrasts are numerically calculated.

FIG. 12 is a graph illustrating the calculation results of a case where a microscopic structure has conduction defects with different heights and the contrasts are numerically calculated.

The graph of FIG. 12 shows an example of results showing how the contrasts change depending on line heights in the patterns in conduction defects. In FIG. 12, two cases are shown as comparison: one case where the signal light and the reference light are not made to interfere with each other; and the other case where the signal light and the reference light interfere are made to interfere with each other. In this numerical calculation, the intensity of the reference light is set at 0.115, and the phase difference between the signal light and the reference light is set at 160°.

According to the calculation results shown in FIG. 12, when the signal light and the reference light are not made to interfere with each other, the positive and negative signs of the contrasts are reversed as the height of the defect varies. In addition, with a certain height of the defect, the contrast becomes zero.

In contrast, when the signal light and the reference light are made to interfere with each other, the use of an appropriate polarization angle, an appropriate polarization phase, intensity, and phase allows the contrast obtained to be always positive. Accordingly, the difference in shape among defects never results in a state where positive and negative contrasts exist in a mixed manner or a state where the contrast becomes extremely low. Instead, a positive contrast can always be detected. Consequently, more microscopic defects can be checked irrespective of the shape of a defect.

Next, description will be given of another pattern inspection method according to an embodiment of the invention.

Figure 13:
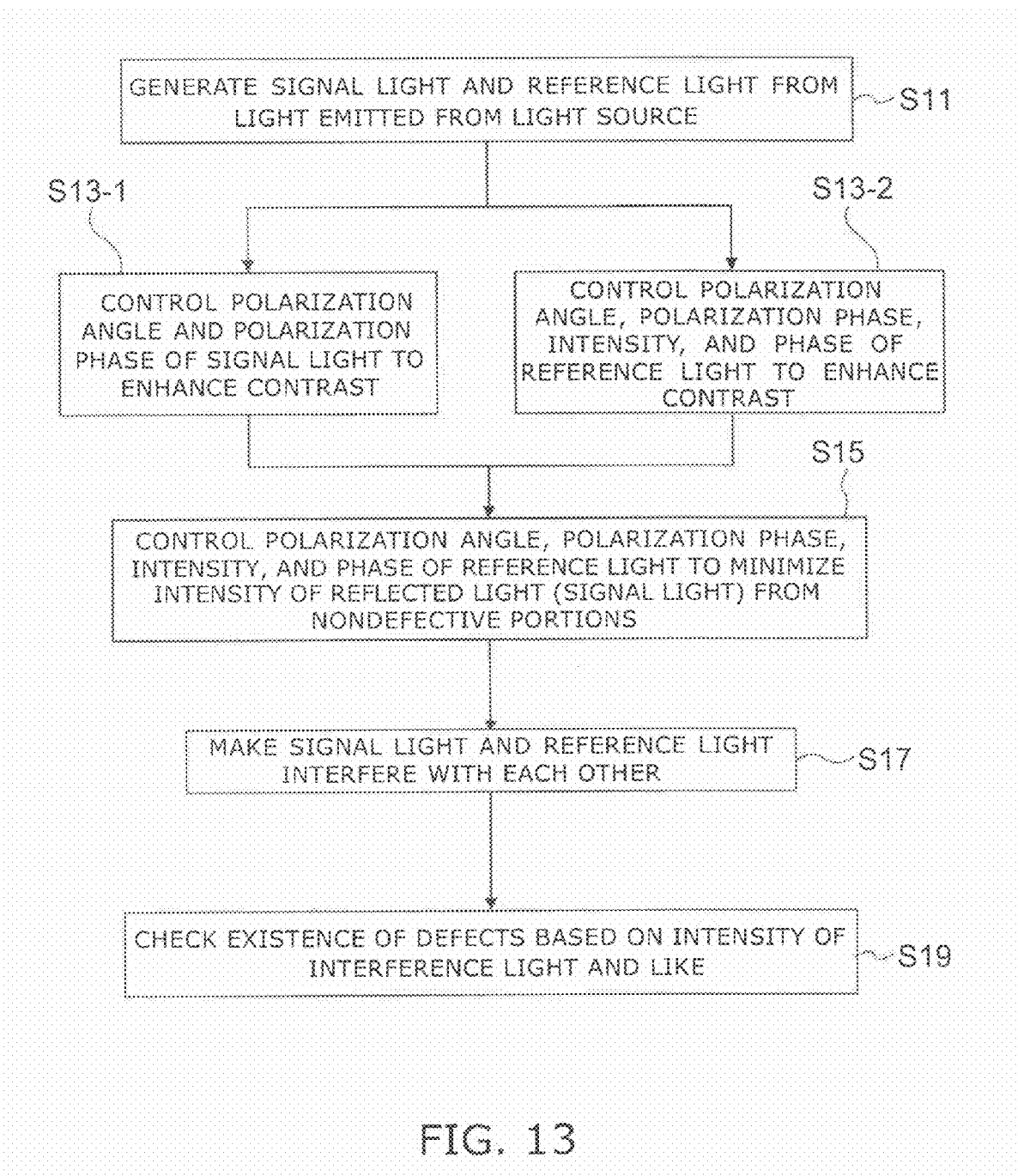
FIG. 13 is a flowchart illustrating another pattern inspection method according to the embodiment.

FIG. 13 is a flowchart illustrating the another pattern inspection method according to the embodiment.

Firstly, signal light and reference light are generated from light emitted from a light source (step S11). As described earlier by referring to FIG. 8, the signal light and the reference light may be generated by splitting light emitted from a single light source into two optical paths. Alternatively, as described earlier by referring to FIG. 9, the signal light and the reference light may be generated from light emitted from respective two light sources.

Subsequently, the polarization angle and polarization phase of the signal light are controlled to enhance the contrast (step S13-1). If light emitted from a single light source is split into two optical paths in this process, the polarization angle and polarization phase of the signal light can be controlled by controlling the polarization angle and polarization phase of the light before the light is split into two optical paths. On the other hand, if two light sources emit respective lights, the polarization angle and polarization phase of the signal light can be controlled by controlling the polarization angle and polarization phase of the light emitted from the light source designed to emit signal light.

In addition, the polarization angle, polarization phase, intensity, and phase of the reference light are controlled to enhance the contrast (step S13-2).

Subsequently, the polarization angle, polarization phase, intensity, and phase of the reference light are controlled to minimize the intensity of the reflected light (signal light) from nondefective portions (step S15).

Subsequently, the reflected light (signal light) from the pattern and the reference light that has been controlled of the polarization angle, polarization phase, intensity, and phase are made to interfere with each other (step S17).

Subsequently, on the basis of the intensity of the interference light and the like, existence of defects is checked (step S19).

According to the pattern inspection method, the contrast concerning a defect can be enhanced. In addition, the enhanced contrast can be obtained in a single inspection. In addition, the higher contrast can be obtained irrespective of the type, the material, and the shape of a defect. Moreover, defects different in type, material, and shape of defects do not cause positive and negative contrast to exist in a mixed manner. In addition, the light-interference conditions do not lower the contrast down to an extremely low level. Thus, a positive contrast can always be obtained. Accordingly, more microscopic defects can be checked.

Next, description will be given of a method of manufacturing a structure according to an embodiment of the invention. A pattern is formed on a surface of the structure.

The method of manufacturing a structure on whose surface a pattern is formed according to the embodiment employs the pattern inspection apparatus and pattern inspection methods of the above-described embodiments. Accordingly, the method of manufacturing a structure on whose surface a pattern is formed according to the embodiment includes a process of forming a pattern on a surface of a structure, and a process of inspecting the pattern by use of the pattern inspection apparatus and the pattern inspection method of the embodiments.

The structure to be manufactured is not limited to a particular kind. The manufacturing method of the embodiment can be employed in the manufacturing of a wide variety of products with patterns formed on the surface. For example, the manufacturing method can be employed when print circuit boards or the like are manufactured. The manufacturing method can be employed in the manufacturing of a structure with a microscopic pattern formed on the surface (microscopic structure). In addition, the manufacturing method can be employed in the manufacturing of a structure with a pattern formed at a pitch shorter than the wavelength of the light to be used in the inspection, and in the manufacturing of a structure that needs an inspection to check defects with a size smaller than the wavelength of the light to be used in the inspection.

Some examples of the structure with a microscopic pattern formed on the surface (microscopic structure) are wafers (semiconductor devices), flat-display panels, photomasks used in a lithography process (reticles), micromachines used in the field of MEMSs, precision optics. The structure with a microscopic pattern is not limited to these mentioned above. The manufacturing method can be employed in the manufacturing of a wide variety of products with microscopic patterns formed on the surfaces.

Description will be given below of a method of manufacturing a semiconductor device as an example.

The method of manufacturing a semiconductor device is performed by repeating plural processes such as a cleaning process, a heat-treatment process, an impurity-introduction process, a diffusing process, a flattening process, and a process to form a pattern on a surface of a substrate (wafer) by forming a film, applying resist, exposure, development, etching, removing the resist, and the like. In the method of manufacturing a structure on whose surface a pattern is formed according to the embodiment (here, a method of manufacturing a semiconductor device), the pattern inspection apparatus and the pattern inspection method of the above-described embodiments are used in an inspection process where the pattern formed on the surface of a substrate (wafer) is checked.

Accordingly, more microscopic defects can be checked, so that the accuracy of inspection patterns can be improved significantly. Consequently, the qualities of the products can be improved.

Note that, techniques that have been known can be employed in the processes where none of the pattern inspection apparatus and the pattern inspection method of the above-described embodiments are involved. Descriptions of these known techniques will not be given.

Various embodiments of the invention have been described thus far. The invention, however, is not limited to the above-described embodiments.

There may be a case where those skilled in the art make appropriate alterations in design to the embodiments. Such altered embodiments are within the scope of the invention as long as the altered embodiments have features of the invention.

For example, the shape, the number, and the location of each element included in any of the pattern inspection apparatus 1, the pattern inspection apparatus 20, and the pattern inspection apparatus 30 are not limited to those described, and can be altered if necessary.

In addition, the elements in the embodiments can be combined together as long as the combination is possible. Such a combination stays within the scope of the invention as long as the combination includes features of the invention.

While certain embodiments have been described, these embodiments have been presented by way of example only, and are not intended to limit the scope of the inventions. Indeed, the novel apparatuses and methods described herein may be embodied in a variety of other forms; furthermore, various omissions, substitutions and changes in the form of the apparatuses and methods described herein may be made without departing from the spirit of the inventions. The accompanying claims and their equivalents are intended to cover such forms or modifications as would fall within the scope and spirit of the invention.

The invention claimed is:

1. A pattern inspection apparatus comprising:
   a light source;
   a beam splitter configured to split a light emitted from the light source into a first optical path and a second optical path;
   a first optical system provided on the first optical path, the first optical system delivering the light to a first pattern and delivering a first reflected light from the first pattern;
   a second optical system provided on the second optical path, the second optical system delivering the light to a second pattern and delivering a second reflected light from the second pattern, the second pattern having an identical shape and dimensions to the first pattern, and the light delivered to the second pattern not overlapping with the light delivered to the first pattern;
   a polarization controller provided on at least one of the first optical path and the second optical path, the polarization controller controlling a polarization angle and a polarization phase, and the polarization controller performing a control so that an intensity of the first reflected light and an intensity of the second reflected light are substantially equal to each other;
   a phase controller provided on at least one of the first optical path and the second optical path, and performing a control so that a phase of the first reflected light and a phase of the second reflected light are inverted from each other; and
   a detector configured to detect a light produced by superposing the first reflected light and the second reflected light one upon the other in the beam splitter so that the first reflected light and the second reflected light are made to interfere with each other.

2. The apparatus according to claim 1 further comprising a second polarization controller provided on a light path between the light source and the beam splitter, and performing a control so that the light emitted from the light source is linearly polarized.

3. The apparatus according to claim 1 further comprising a first light-irradiation controller provided on the first optical path and changing a light-irradiation position.

4. The apparatus according to claim 1 further comprising a second light-irradiation controller provided on the second optical path and changing a light-irradiation position.

5. The apparatus according to claim 1 further comprising a holder unit to hold a substrate on which the second pattern is formed.

6. The apparatus according to claim 1 wherein the second pattern is a pattern with no defects.

7. The apparatus according to claim 1 wherein the light source is provided in plurality.

8. A pattern inspection method comprising:
   splitting a light emitted from a light source into a first optical path and a second optical path;
   generating a first reflected light from a first pattern being an inspection target by irradiating the first pattern with the light via the first optical path;
   generating a second reflected light from a second pattern by irradiating the second pattern with the light via the second optical path, the second pattern having an identical shape and dimensions to the first pattern, and the light delivered to the second pattern not overlapping with the light delivered to the first pattern;

performing a control so that an intensity of the first reflected light is substantially equal to an intensity of the second reflected light by controlling a polarization angle and a polarization phase, and that a phase of the first reflected light and a phase of the second reflected light are inverted from each other;

making the controlled first reflected light and the controlled second reflected light interfere with each other; and checking existence of defects on the basis of an intensity of the interference light.

9. The method according to claim 8 wherein the second pattern is a pattern with no defects.

10. The method according to claim 8 wherein the first pattern is formed on an object to be inspected and the second pattern is formed on a substrate that is different from the object to be inspected.

* * * * *